US010601247B2

(12) United States Patent
Lausch et al.

(10) Patent No.: US 10,601,247 B2
(45) Date of Patent: Mar. 24, 2020

(54) SYSTEM FOR THE WIRELESS TRANSMISSION OF ENERGY AND/OR SIGNALS, THE CONVERSION OF ENERGY AND/OR SIGNALS INTO OTHER FORMS OF ENERGY AND/OR FORMS OF SIGNAL, AND THE APPLICATION AND DETECTION OF SAME IN PERIPHERAL REGIONS OF SAID SYSTEM

(71) Applicant: Fraunhofer-Gesellschaft zur Foerderung der angewandten Forschung e. V., Munich (DE)

(72) Inventors: Holger Lausch, Jena (DE); Michael Brand, Jena (DE); Michael Arnold, Jena (DE)

(73) Assignee: FRAUNHOFER-GESELLSCHAFT ZUR FOERDERUNG DER ANGEWANDTEN FORSCHUNG E. V., Munich (DE)

( * ) Notice: Subject to any disclaimer, the term of this patent is extended or adjusted under 35 U.S.C. 154(b) by 0 days.

(21) Appl. No.: 15/755,974

(22) PCT Filed: Aug. 26, 2016

(86) PCT No.: PCT/DE2016/100384
§ 371 (c)(1),
(2) Date: Feb. 27, 2018

(87) PCT Pub. No.: WO2017/036454
PCT Pub. Date: Mar. 9, 2017

(65) Prior Publication Data
US 2019/0044380 A1    Feb. 7, 2019

(30) Foreign Application Priority Data
Aug. 28, 2015 (DE) ........................ 10 2015 114 406

(51) Int. Cl.
*H04B 5/00* (2006.01)
*A61B 5/00* (2006.01)
(Continued)

(52) U.S. Cl.
CPC ............ *H02J 50/10* (2016.02); *A61B 5/0015* (2013.01); *A61B 5/0031* (2013.01); *A61B 5/01* (2013.01);
(Continued)

(58) Field of Classification Search
CPC ......... H02J 50/00; H02J 50/10; A61B 5/0015; A61B 5/0031; A61B 5/01; A61B 5/1114;
(Continued)

(56) References Cited

U.S. PATENT DOCUMENTS

| 4,195,367 A | 4/1980 | Kraus |
| 7,867,235 B2 | 1/2011 | Fell et al. |

(Continued)

FOREIGN PATENT DOCUMENTS

| DE | 102010047738 A1 | 3/2012 |
| DE | 202012000166 U1 | 4/2013 |

(Continued)

*Primary Examiner* — Hal Kaplan
(74) *Attorney, Agent, or Firm* — Abel Schillinger, LLP

(57) ABSTRACT

Discloses is a system for the wireless transmission of energy and/or signals between spatially-separated regions with no electrically-conductive connection, the conversion of energy and/or signals into other forms of energy and/or forms of signal, and the application and/or detection of same in at least one peripheral region of said system. The system allows a wireless transmission of energy between at least two spatially-separated regions without an electrically-conductive connection, energy being supplied to at least one of these regions, transmitted to at least one additional region in a wireless manner, converted on demand into other forms of energy, and applied in a peripheral region of said system.

(Continued)

Signals can be transmitted at the same time as energy is being transmitted.

20 Claims, 15 Drawing Sheets

(51) Int. Cl.
*A61B 5/01* (2006.01)
*H02J 50/00* (2016.01)
*H02J 50/10* (2016.01)
*A61F 2/32* (2006.01)
*A61N 1/378* (2006.01)
*A61B 5/11* (2006.01)
*A61F 2/28* (2006.01)
*A61F 2/30* (2006.01)
*A61F 2/48* (2006.01)
*A61F 2/46* (2006.01)
*A61B 17/80* (2006.01)
*A61B 10/00* (2006.01)
*A61B 17/00* (2006.01)

(52) U.S. Cl.
CPC .............. *A61B 5/1114* (2013.01); *A61F 2/32* (2013.01); *A61N 1/3787* (2013.01); *H04B 5/0031* (2013.01); *H04B 5/0037* (2013.01); *H04B 5/0081* (2013.01); *A61B 17/80* (2013.01); *A61B 2010/009* (2013.01); *A61B 2017/00221* (2013.01); *A61B 2562/0219* (2013.01); *A61B 2562/0223* (2013.01); *A61F 2002/2864* (2013.01); *A61F 2002/3067* (2013.01); *A61F 2002/30079* (2013.01); *A61F 2002/30087* (2013.01); *A61F 2002/30668* (2013.01); *A61F 2002/465* (2013.01); *A61F 2002/4651* (2013.01); *A61F 2002/482* (2013.01); *H02J 50/00* (2016.02)

(58) Field of Classification Search
CPC .............. A61B 17/80; A61B 2010/009; A61B 2017/00221; A61B 2562/0219; A61B 2562/0223; A61F 2/32; A61F 2002/30079; A61F 2002/30087; A61F 2002/30668; A61F 2002/3067; A61F 2002/465; A61F 2002/4651; A61F 2002/482; A61F 2002/2864; A61N 1/3787; H04B 5/0031; H04B 5/0037; H04B 5/0081
USPC ........................................................ 307/104
See application file for complete search history.

(56) References Cited

U.S. PATENT DOCUMENTS

| | | |
|---|---|---|
| 8,512,264 B1 | 8/2013 | Asfora |
| 2007/0004994 A1 | 1/2007 | Sherman |
| 2007/0293912 A1 | 12/2007 | Cowan et al. |
| 2011/0101788 A1 | 5/2011 | Sun et al. |
| 2012/0053633 A1 | 3/2012 | Stauch |
| 2014/0107542 A1 | 4/2014 | Schubert et al. |

FOREIGN PATENT DOCUMENTS

| | | |
|---|---|---|
| EP | 1738716 B1 | 4/2012 |
| WO | 2012116038 A1 | 8/2012 |

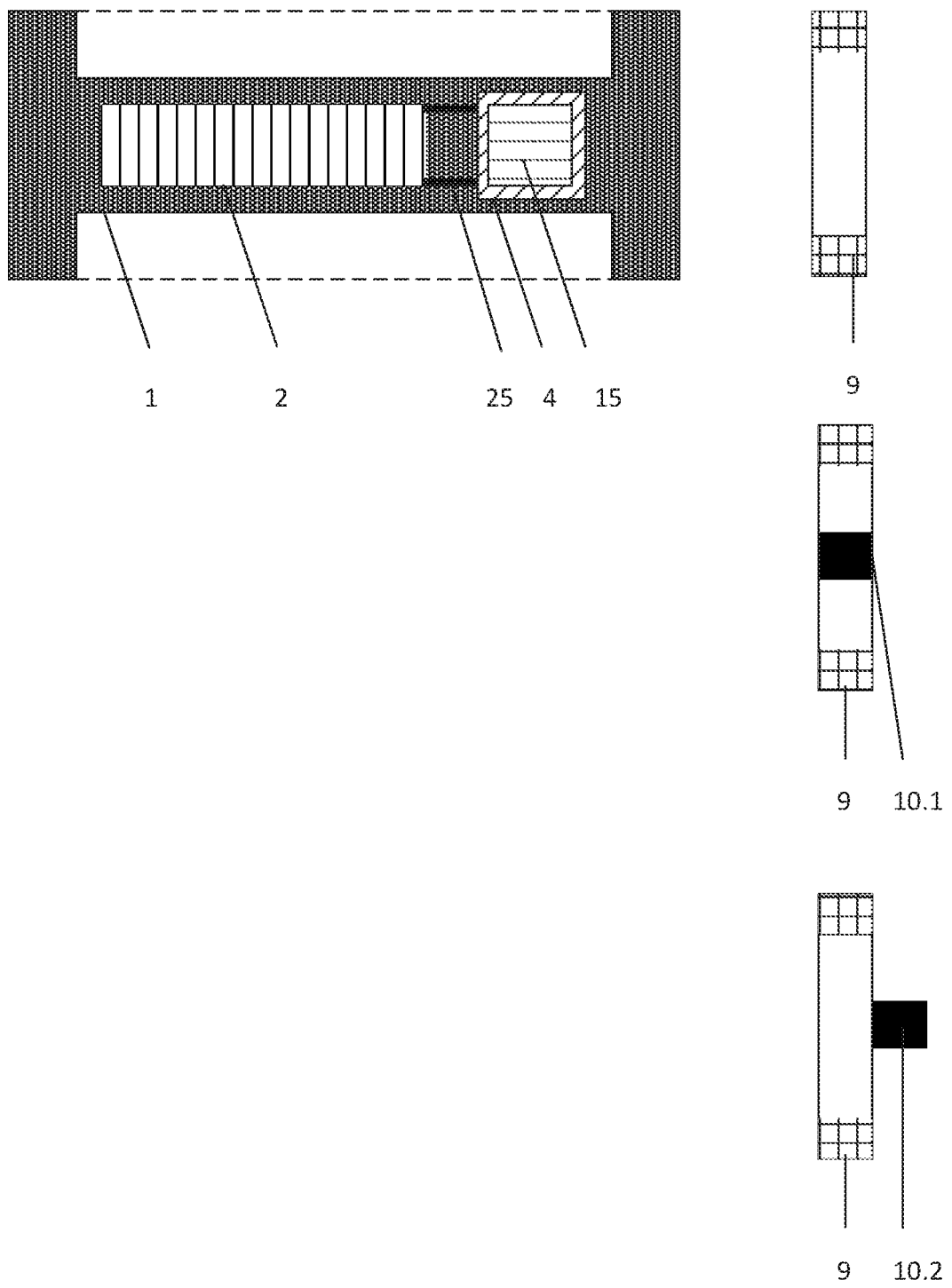
Fig. 1.1

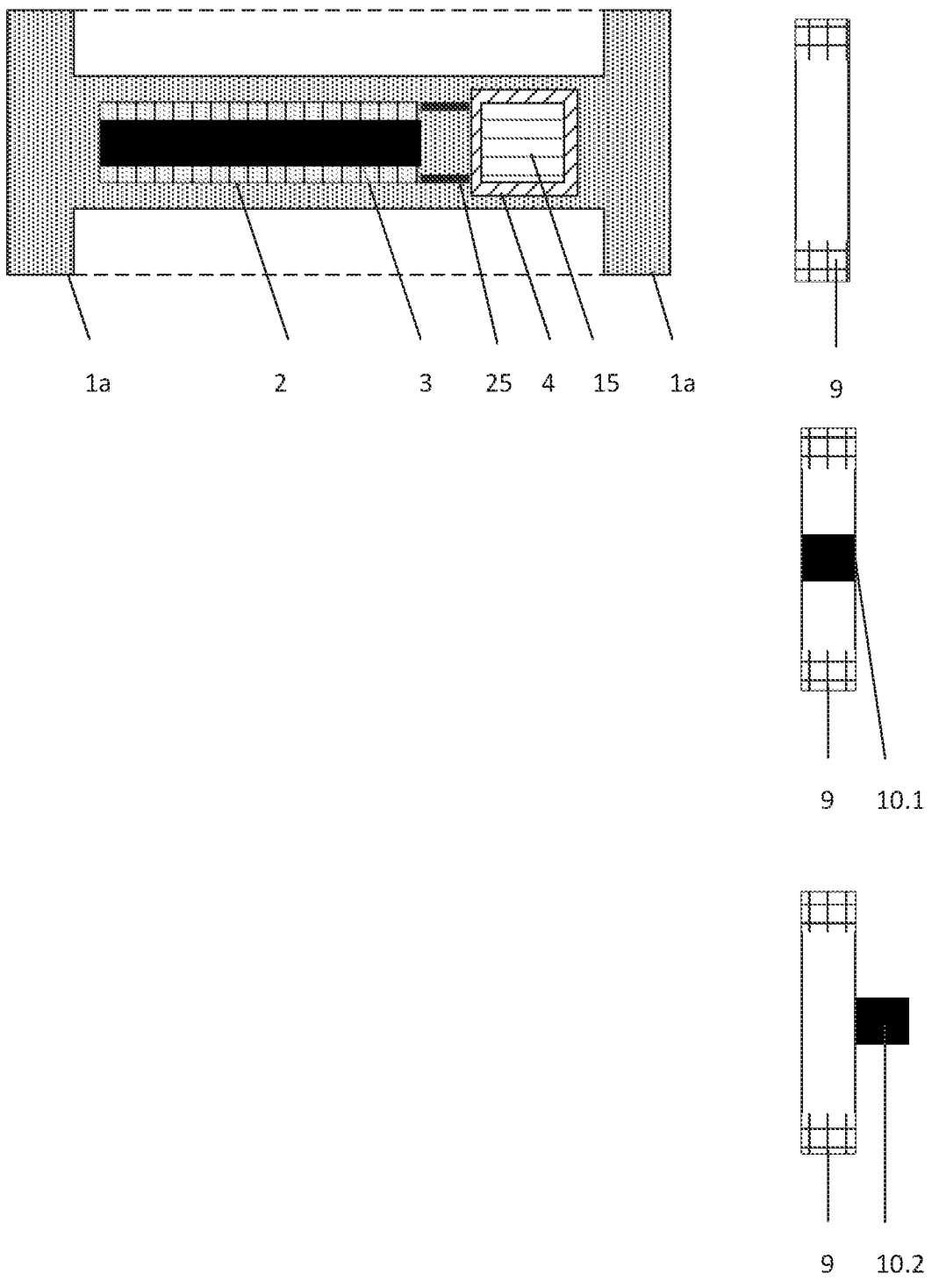
Fig. 1.2

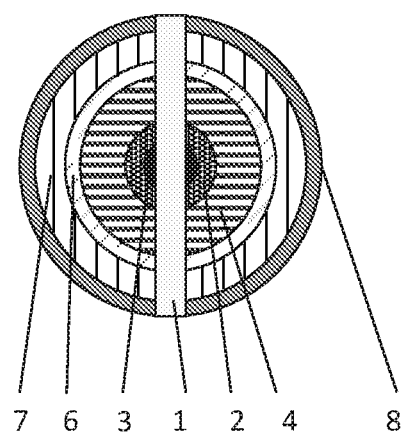
7 6 3 1 2 4 8
Fig. 2.1
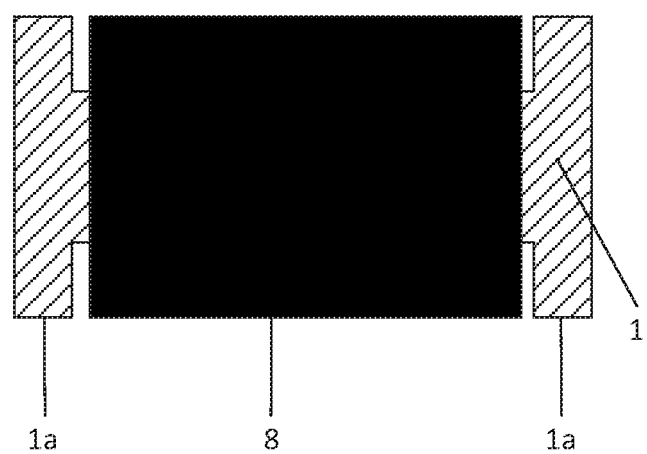
1a 8 1a
Fig. 2.2

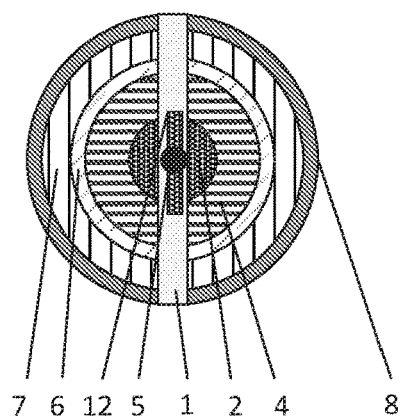
7 6 12 5 1 2 4     8
Fig. 3.1
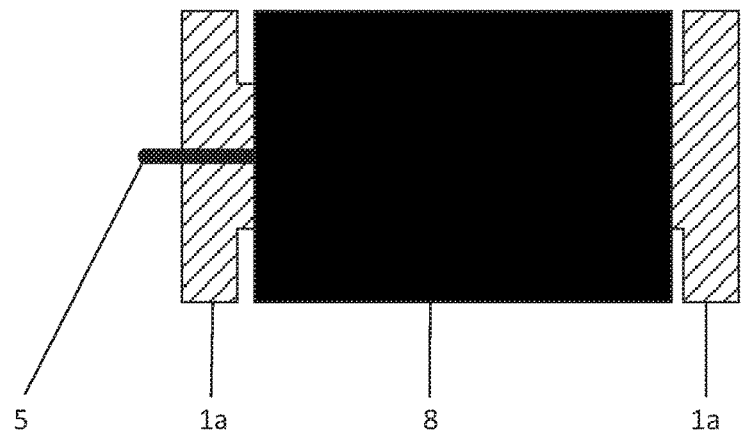
5    1a    8    1a
Fig. 3.2
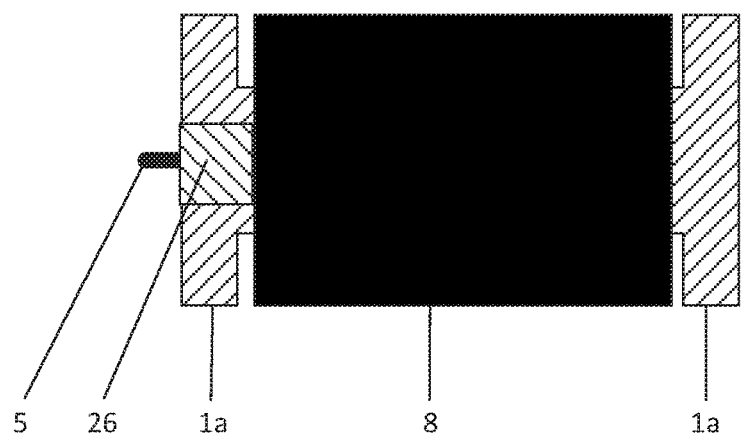
5   26   1a    8    1a
Fig. 3.3

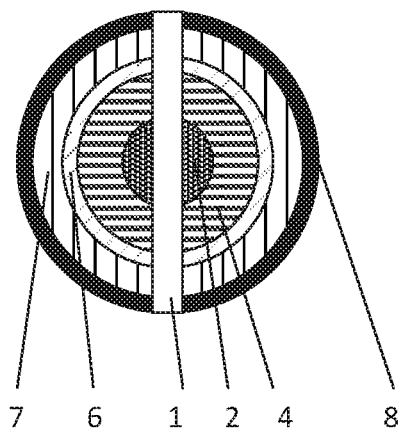
7  6  1  2  4    8
Fig. 4.1
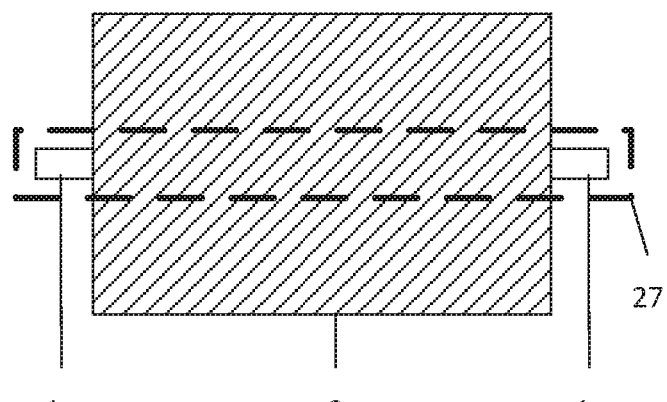
1a              8              1a
Fig. 4.2
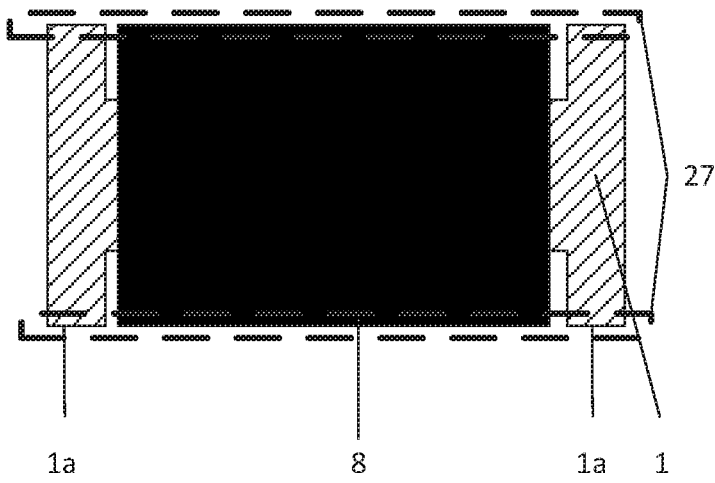
1a              8              1a  1
Fig. 4.3

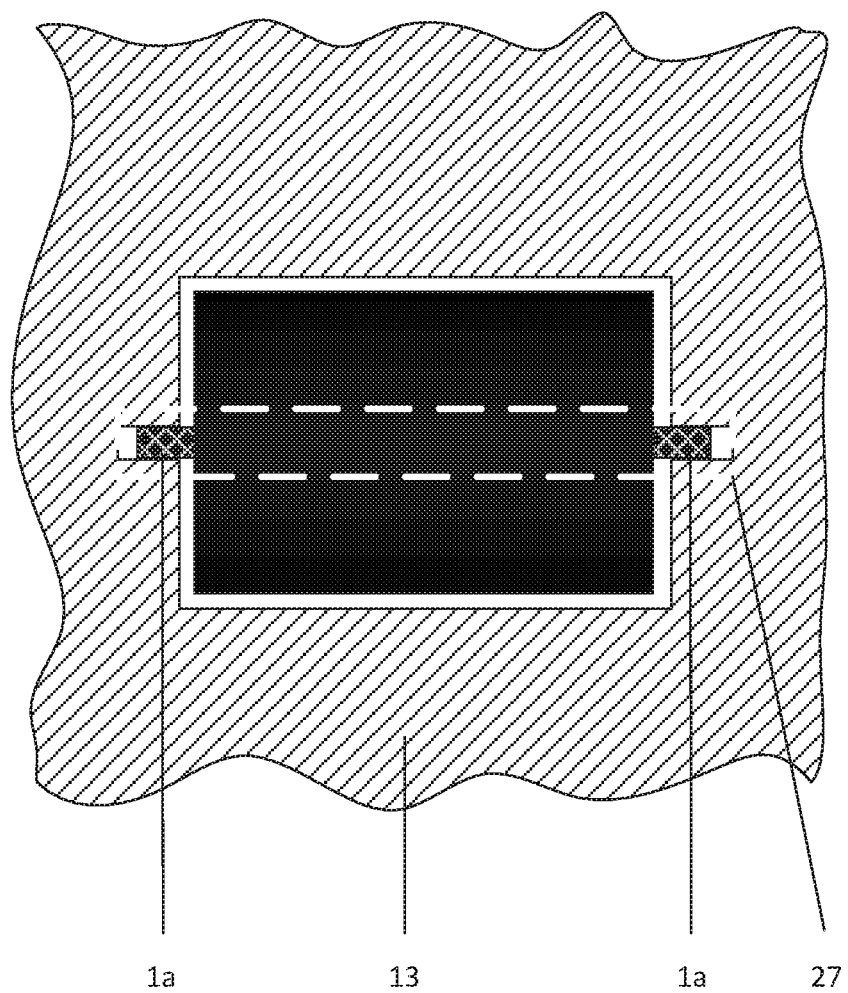
Fig. 4.4

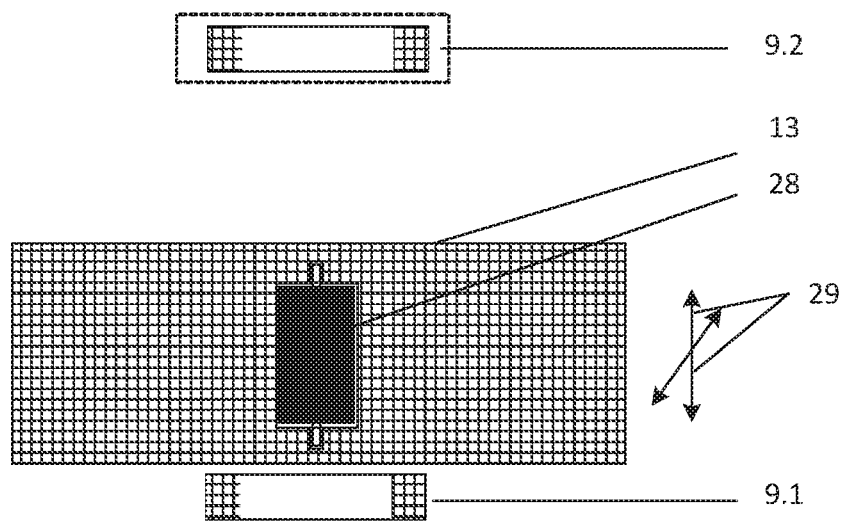
Fig. 5.1
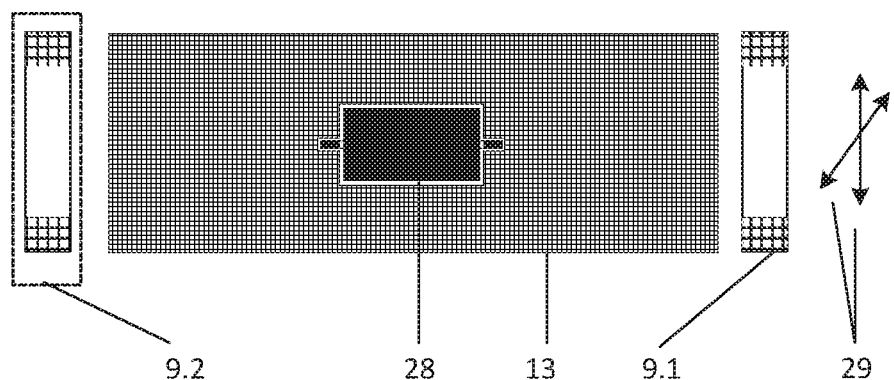
Fig. 5.2

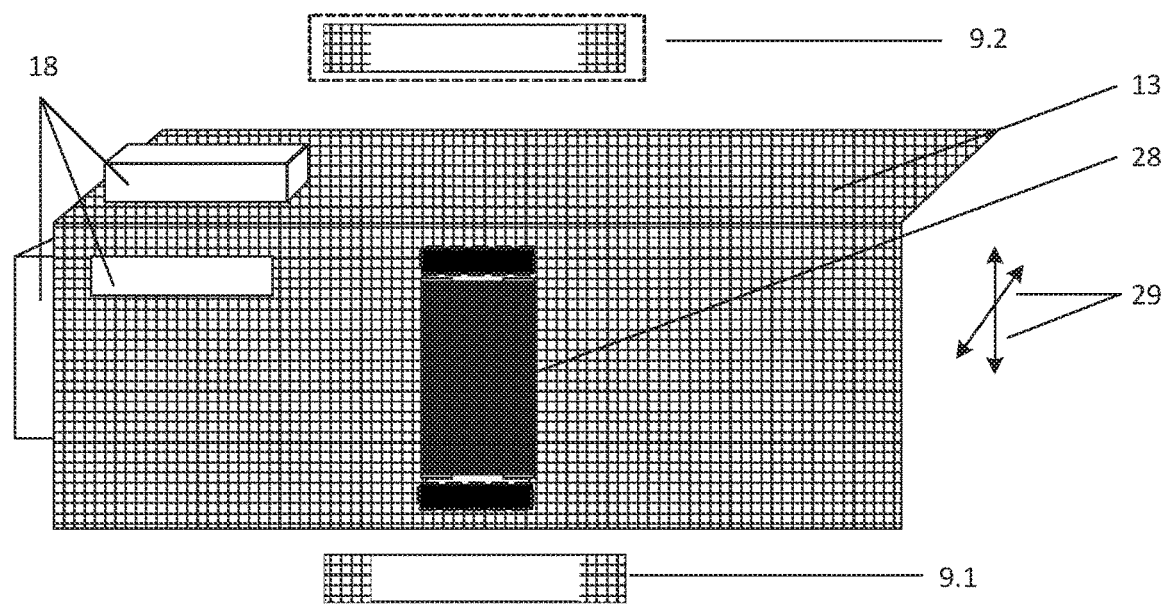
Fig.5.3
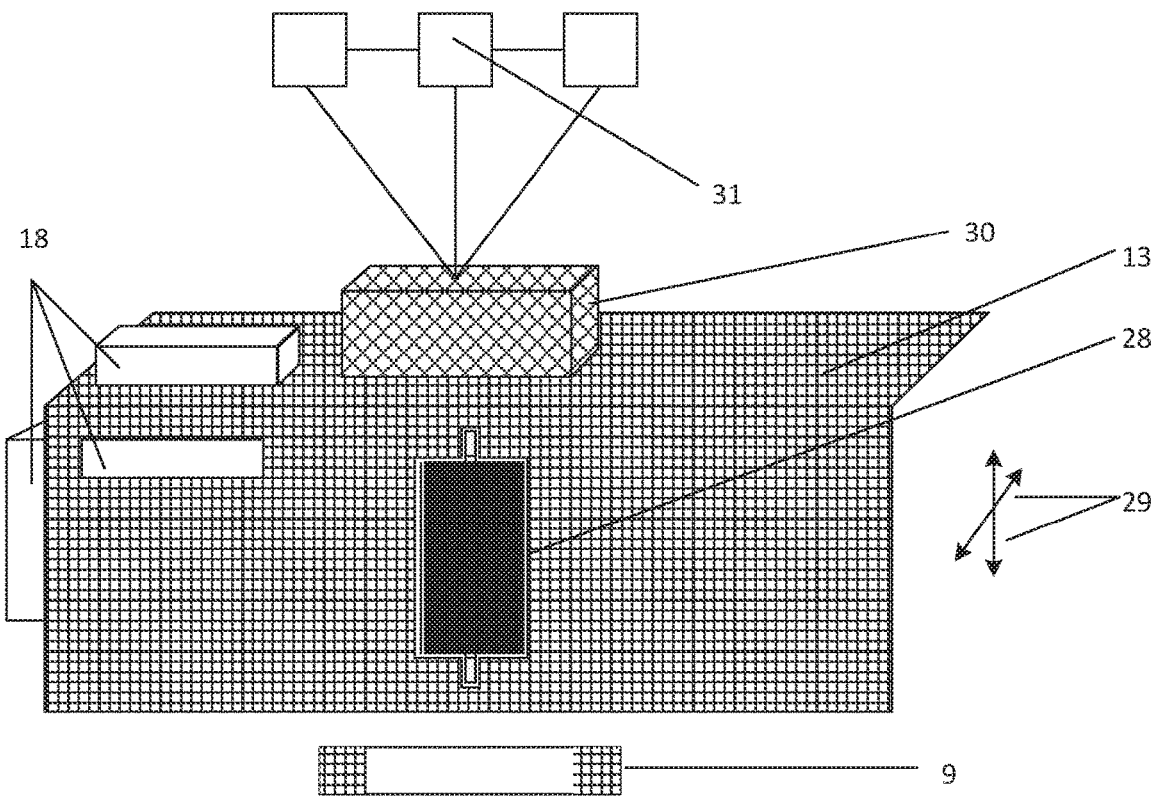
Fig. 5.4

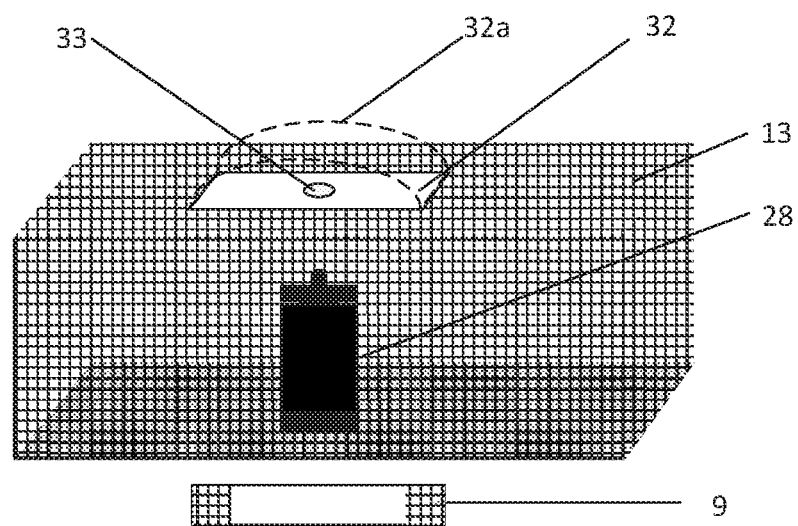
Fig. 6.1

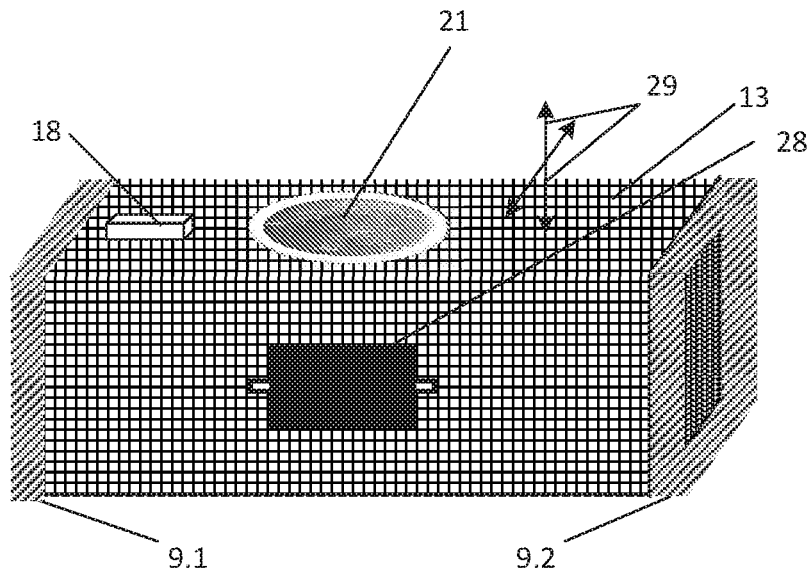
Fig. 7.1
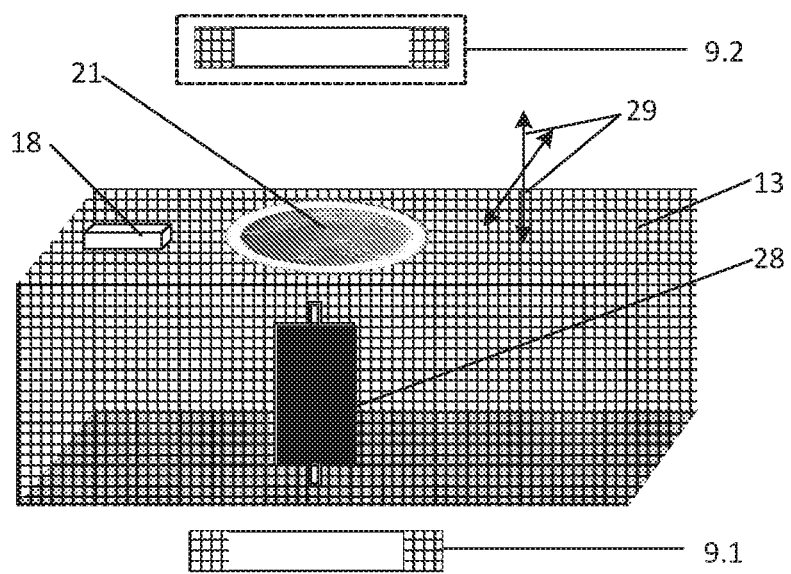
Fig. 7.2

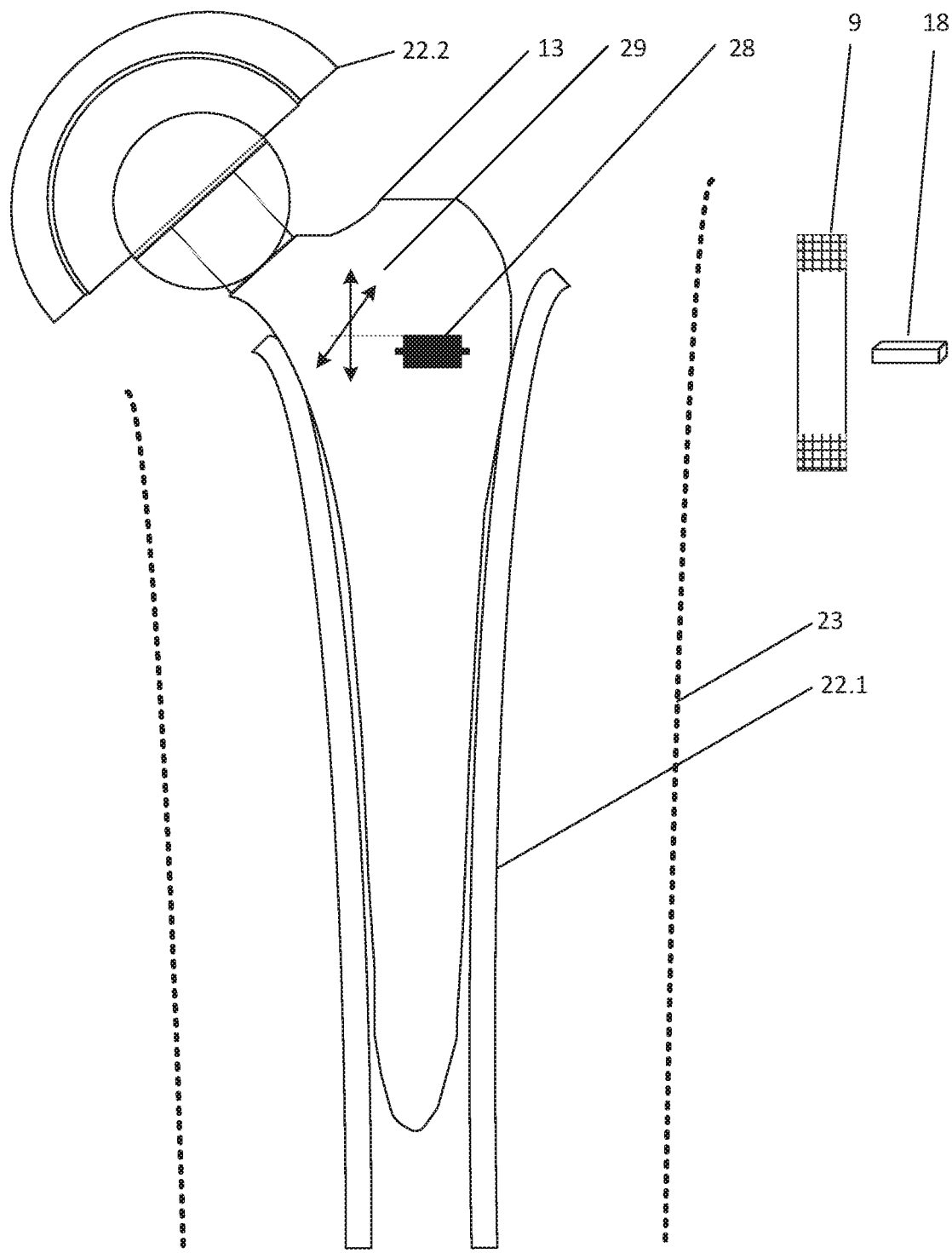
Fig. 8.1

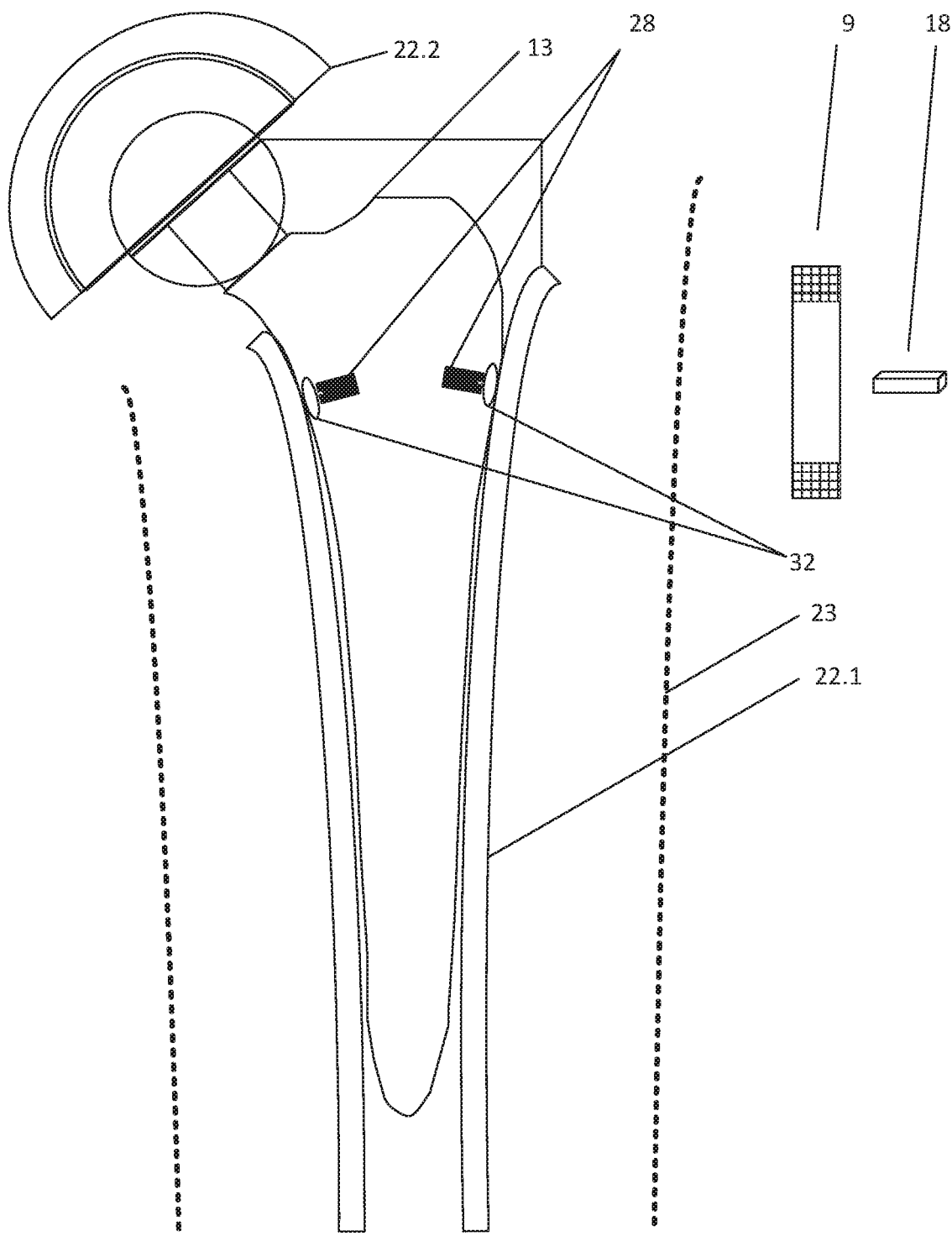
Fig. 8.2

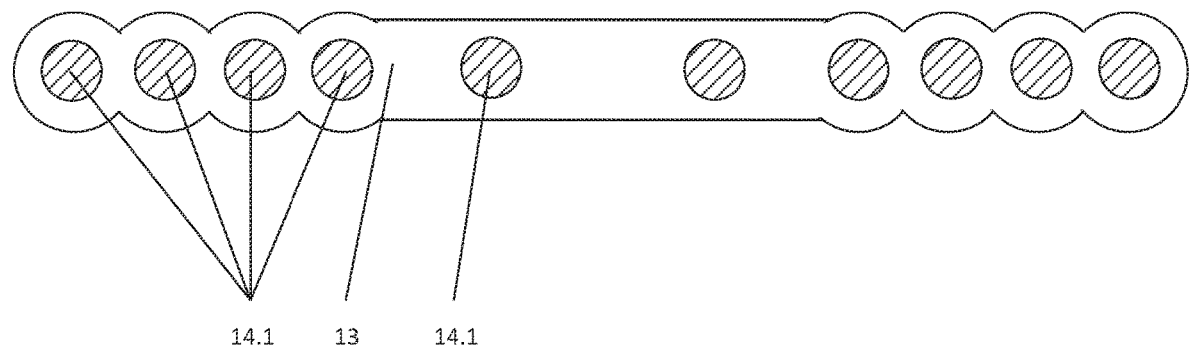
Fig. 9.1
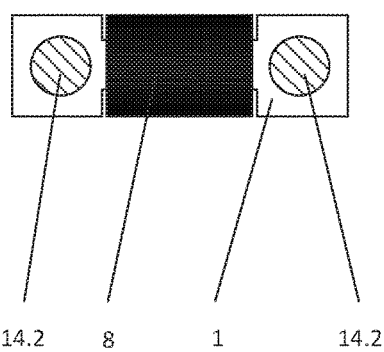
Fig. 9.2
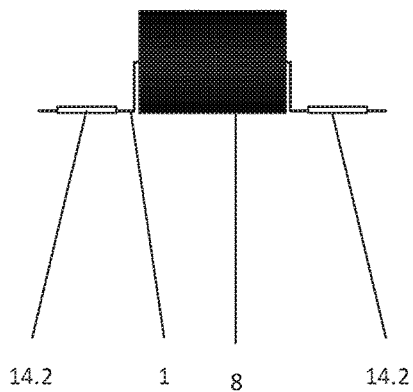
Fig. 9.3

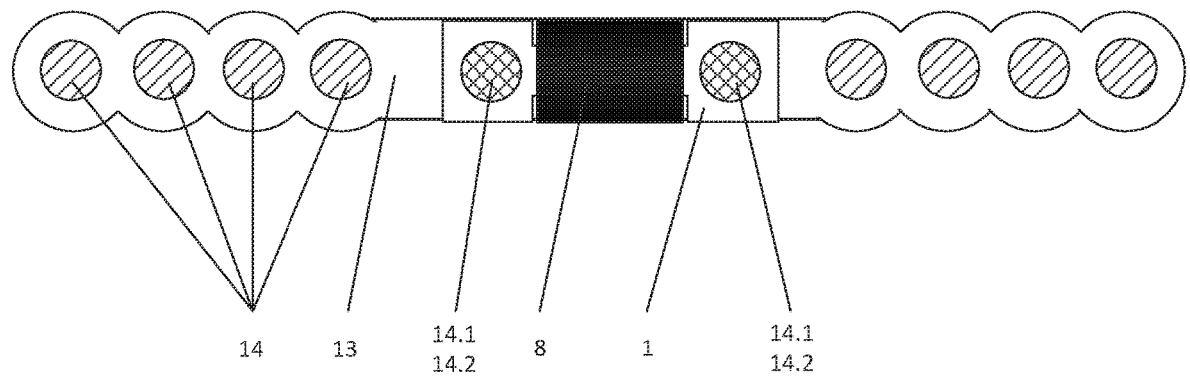
Fig. 9.4
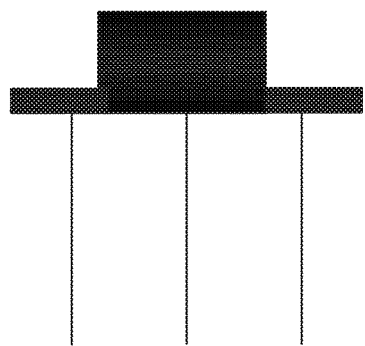
Fig. 9.5
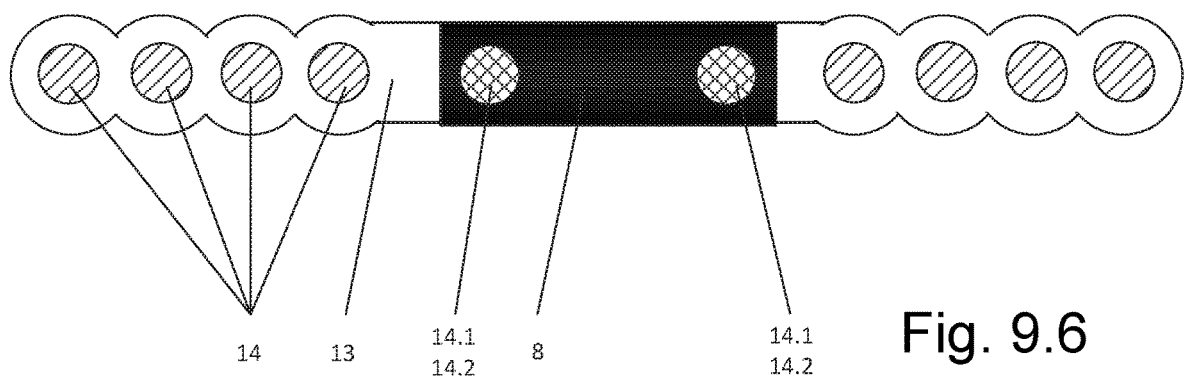
Fig. 9.6

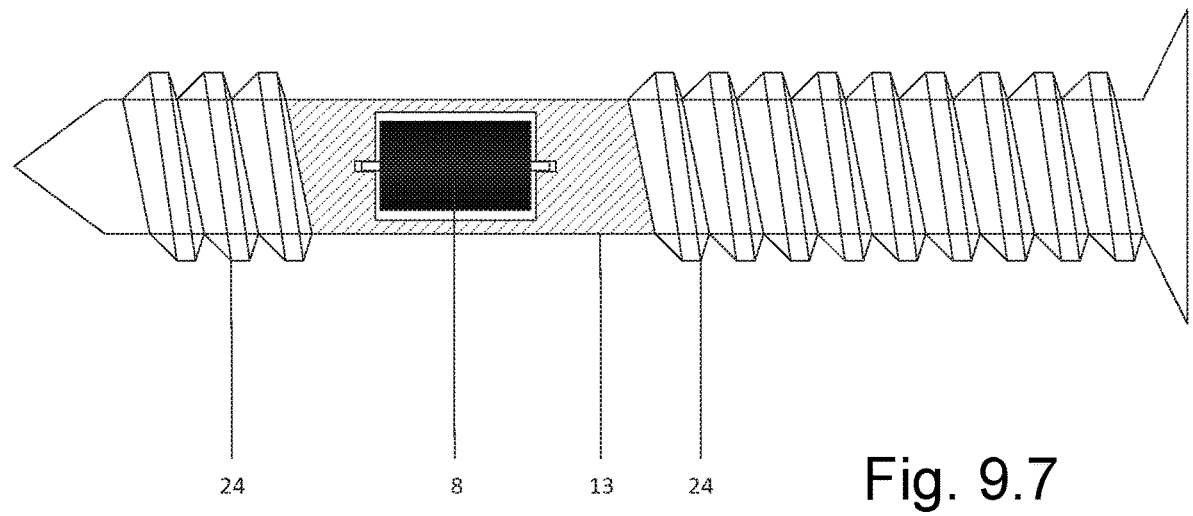
Fig. 9.7
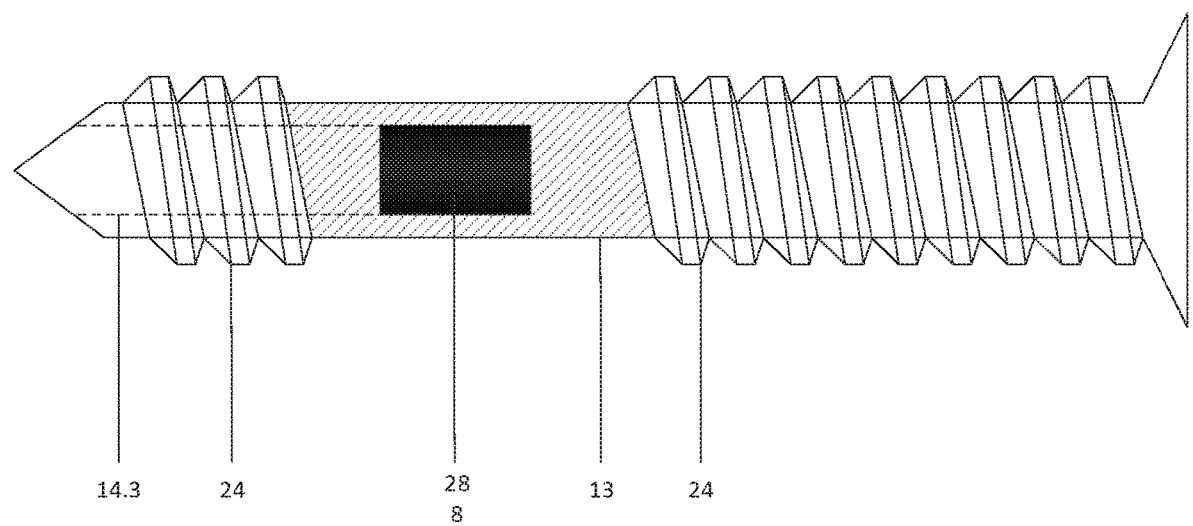
Fig. 9.8

SYSTEM FOR THE WIRELESS TRANSMISSION OF ENERGY AND/OR SIGNALS, THE CONVERSION OF ENERGY AND/OR SIGNALS INTO OTHER FORMS OF ENERGY AND/OR FORMS OF SIGNAL, AND THE APPLICATION AND DETECTION OF SAME IN PERIPHERAL REGIONS OF SAID SYSTEM

BACKGROUND OF THE INVENTION

1. Field of the Invention

The invention relates to a system for the wireless transmission of energy and/or signals between physically separate regions without an electrically conductive connection, the conversion of the energy and/or signals into other energy forms and/or signal forms and the application and/or detection thereof in at least one peripheral region of the system.

Advantageously, the system allows a wireless energy transmission between at least two physically separate regions without an electrically conductive connection, with energy being supplied to at least one of these regions and being transmitted wirelessly to at least one further region, converted into other energy forms as required and applied in a peripheral region of the system.

Advantageously, it is also possible for signals to be transmitted at the same time as energy is transmitted. The signals can firstly be generated in a peripheral region of the system by physical, biological or chemical processes or states and detected and converted by the system, but can secondly also be produced independently of the system, supplied to the system and transmitted wirelessly to the respective other region.

The system allows in particular mechanical, acoustic, thermal, optical and other physical or chemical gradients (vibrations, sound waves or heat) to be achieved and coupled or transmitted to peripheral regions of the system. Advantageously, a peripheral region of the system is a shaped body or part of a shaped body in this case. The shaped body may be either part of the system or part of external structures and systems with which the system is associated. Elements of the system can be introduced directly into a shaped body or arranged on a surface thereof, able to be screwed on and/or injection-molded on or welded on.

In medical applications, the shaped body may be an implant or an osteosynthetic component/plate or a screw or a pin or an orthesis. In the case of building applications, the shaped body may be a structural member or a supporting structure, masonry or a reinforcing element. In the vehicle sector, the shaped body may be a chassis or a frame or a part, for example. In this case too, the actuating/sensory system component may be introduced directly into a shaped body or arranged on the surface thereof, able to be screwed on and/or injection-molded on or welded on.

2. Discussion of Background Information

In particular in the case of implants, it may be advantageous to employ vibrations or sound waves for damping analysis at the bone/implant contact zone for loosening detection purposes or for improved ingrowth in the tissue as stimulation or to encourage movement and hence also metabolism in the target tissue, including or excluding the neighboring tissue, to prevent stiffening. Thermal energy can be used to initiate mechanical manipulations at the transitions from implants to the tissue, for example by means of shape memory materials, inflatable bags or by means of thermal expansion, and to initiate chemical reactions to release active substances.

In this case, it is known practice to deflect masses in conjunction with electromagnetic alternating fields, a deflection being effected between two reversal points. In order to obtain adequate results, appropriately high masses of bodies to be deflected are required. The movements give rise to wear, which is undesirable. Moreover, undesirable inertia effects can arise with excessively negative or positive accelerations and associated material/tissue fatigue and also corresponding damage as a result of expansion and compression processes.

Moreover, a deflection can take place exclusively in the region of a few hertz. Without the analysis at higher frequencies, particular statements about the state of an implant cannot be made, for example detailed statements regarding the strength of the anchoring of said implant in the tissue and in regard to the influence of stimulation effects on the ingrowth behavior.

It is therefore an object of the invention to provide simple, robust and manipulation-proof opportunities for a transmission, conversion and application of energy and signals that require no complex open-loop and closed-loop control systems at the location of application, that allow a wireless transmission of energy and signals between physically separate regions that are not electrically conductively connected, and hence a system operable and controllable wirelessly exclusively from an external region, and that realize a conversion of the energy into other energy types such that this requires no freely mobile, oscillating or sprung masses, so that use for a wide variety of applications, in particular for implants or prostheses, is advantageous.

It is in particular also an object of the invention to provide opportunities that allow different energy forms to be converted into one another as required and that allow use of these energy forms for spatially defined manipulation of peripheral regions of the system and/or for signal transmission purposes. The latter also allows use of the system for detection purposes and for monitoring process and state variables in peripheral regions of the system. Preferably, kinetic, thermal, chemical or electromagnetic energy forms are suitable for the manipulation of peripheral regions of the system.

SUMMARY OF THE INVENTION

The present invention provides a system for the wireless transmission of energy and/or signals between physically separate regions without electrically conductive connections, the conversion of the energy and/or signals into other energy forms and/or signal forms and the application and/or detection thereof in at least one peripheral region of the system. The system comprises at least one first transducer element, in particular a first electrical coil or a magnetizable material or a movable permanent magnet, by which magnetic alternating fields and/or magnetic signal forms are generable and/or detectable, the first transducer element being arranged in a first region, and at least one second transducer element, in particular a second electrical coil, that allows reciprocal, unidirectional or bidirectional conversion of energy of the magnetic alternating fields and/or of the magnetic signal forms into electrical energy and/or electrical signal forms, as well as a third transducer element that allows reciprocal, unidirectional or bidirectional conversion of the electrical energy and/or electrical signal forms into mechanical energy, in particular in the form of vibrations or sound waves, the second transducer element and the third transducer element being arranged in a further region adjacent to the first region, or at least one second transducer element, in particular a second electrical coil, by which the energy of the magnetic alternating fields generable by the first transducer element is convertible into thermal energy by hysteretic heating and/or eddy currents and/or by Joule heating of the second transducer element, as well as a thermal conductor element that forwards the thermal energy to a location of application, the second transducer element and the thermal conductor element being arranged in a further region adjacent to the first region, or at least one second transducer element, in particular a second electrical coil, that allows reciprocal, unidirectional or bidirectional conversion of energy of the magnetic alternating fields and/or of the magnetic signal forms into electrical energy and/or electrical signal forms and/or thermal energy, as well as at least one fourth transducer element that is electrically and/or thermally conductively connected to the second transducer element and allows reciprocal, unidirectional or bidirectional conversion of the electrical energy and/or electrical signal forms and/or thermal energy into further energy forms, in particular mechanical energy and/or chemical energy and/or electromagnetic radiation, at least partially, and/or forwards these energy forms, the second transducer element and the fourth transducer element being arranged in a further region adjacent to the first region.

In one aspect of the system, second, third or fourth transducer elements may be fixed alone or together with other transducer elements in a receptacle element and/or the third transducer element may be a piezoelectric transducer element and/or a ferromagnetic core may be arranged on or in a second transducer element and/or the second transducer element and the third transducer element may be directly electrically conductively connected and/or at least one third transducer element may be configured as or may contain a short-circuit path of a coil of the second transducer element.

In another aspect of the system, a fourth transducer element may convert and/or forward at least some of the energy of at least one second transducer element and/or of at least one third transducer element into other energy forms, in particular kinetic, thermal, electromagnetic or chemical energy.

In yet another aspect, the second, third or fourth transducer elements may be arranged in a parallel and/or series arrangement or independently of one another, so that a multiple conversion of magnetic energy into electrical, mechanical, kinetic energy and/or thermal energy is achievable.

In a still further aspect of the system, a first transducer element may be an electrical coil having a ferromagnetic core, the ferromagnetic core being arranged in and/or on the electrical coil and/or a first transducer element may consist of a combination of multiple coils that have one or more associated ferromagnetic cores made of the same or different materials.

In another aspect, a receptacle element may comprise at least one contour element present on it or the receptacle element may be formed from an elastically deformable or acoustically conductive material, in particular from metal or a metal alloy.

In another aspect, at least part of the second transducer element, the third transducer element and/or the fourth transducer element may be enclosed by a shaped body. For example, the shaped body may be a prosthesis, an orthosis, an implant or an osteosynthetic aid and/or the shaped body may comprise at least one associated sensor or sensory-action, preferably porous body and/or the shaped body may comprise at least one receptacle for a (preferably biological) sample present on it.

In another aspect of the system, the first transducer element may provide magnetic fields and signal forms at frequencies in the range of from 10 Hz to 3000 Hz, preferably in the range 175 Hz to 300 Hz.

In another aspect, the first transducer element may comprise at least one electrical coil to which a constant AC voltage is applied and at least one of the second, third or fourth transducer elements may allow the conversion of the energy of the magnetic alternating fields and/or of the magnetic signal forms of the first transducer element into electrical energy and/or electrical signal forms and/or further energy or signal forms such that the last transducer element in a cascade realizes a physical gradient independently of frequency.

In another aspect, the signals generated by at least one of the second, third or fourth transducer elements may be recordable by a sensor, the sensor being arranged in the first region or in a further region that does not contain the transducer elements. For example, the sensor may be a sensor for detecting magnetic fields, in particular a magnetic field sensor or a sensor coil. The sensor coil may coincide with at least one of the electrical coils of the first transducer element.

A system according to the invention is configured such that in at least one first external region at least one first transducer element, in particular an electrical primary coil or a movable permanent magnet, by which a magnetic alternating field is generable and/or by which the energy of a magnetic alternating field is convertible into electrical energy in inverse form is part of the system.

In addition, in at least one second region, which is physically separate from the first region and not electrically conductively connected, at least one second transducer element, in particular at least one electrical coil, is present by which the energy of the magnetic alternating field of the first transducer element is convertible into electrical energy owing to induction and/or, in the inverse form, electrical energy is convertible into magnetic energy and transmittable to the first transducer element and/or detectable by a further sensor. In one advantageous embodiment, the at least one electrical coil has at least one associated ferromagnetic core made of soft magnetic material.

The second transducer element may, in one alternative of the invention, be configured such that the magnetic energy of the first transducer element is convertible into thermal energy, wherein the second transducer element in this case is preferably at least one shorted electrical coil, or an electrical coil provided with an electrical load, that may have one or more associated ferromagnetic cores. The conversion of the energy of the magnetic field of the first transducer element into thermal energy can be effected by means of different conversion mechanisms in this case. First, the energy of the magnetic field of the first transducer element can be converted initially into electrical energy and subsequently, by virtue of Joule heating of the coil and/or of an electrical load connected to the coil, such as a filament, for example, into thermal energy, and secondly, a direct conversion of the energy of the magnetic field into thermal energy by virtue of hysteretic losses during the remagnetization of the core material and/or eddy current losses in the core material and conducting materials in the surroundings of the coil is also possible. On the basis of the chosen core materials and the geometry and dimensioning of the coils and cores, different variants of the second transducer element can be realized with different components of the described conversion processes, depending on the application scenario.

Reciprocal influencing of the utilizable conversion processes is possible. It is thus possible to influence the intensity of the effect of the respective conversion process by means of a particular selection of a core arranged in the electrical coil, as far as the core material and the geometrical dimensioning (shape, volume) are concerned. The dimensioning of the electrical coil by means of wire diameter, number of turns, winding width and winding type can also influence the effect of a second transducer element.

For Joule heating, relatively high electric currents are beneficial. Therefore, high induction voltages and a core made of a highly permeable soft magnetic material are useful. Optimization of the nonreactive resistance of the electrical coil is likewise advantageous, so that the converted power is as high as possible.

For hysteretic heating, large hysteretic losses are needed. Therefore, a core material with high coercive field strengths and high saturation flow density may be beneficial in this case. Remagnetizations and demagnetizations should be possible. To this end, a magnetically semi-hard core material is advantageous. Higher field strengths of the magnetic field of the first transducer element or of a magnetic alternating field generated by means of a second transducer element likewise result in an improved thermal effect. A further influencing parameter is the geometry, e.g. the length/width ratio, of the core, which can be optimized such that the demagnetizing field in the core becomes as small as possible.

Heating by means of eddy currents always occurs in combination with hysteretic heating. Influencing is possible in this case by way of the electrical conductivity of the materials used, the layering to avoid eddy currents as in the case of the transformer and the orientation of the conductive components of the system in relation to the magnetic alternating field.

Additionally, in a further alternative of a system according to the invention, at least one further transducer element may be part of the system. The further transducer element, as third transducer element, can convert electrical energy into kinetic energy, in particular vibrations or sound waves, and/or, in inverse form, kinetic energy into electrical energy and in this case may in particular be a piezoelectric element or a permanent magnet that is held fixedly in a receptacle element.

In a further alternative of the invention, a fourth transducer element may be present on its own or in addition to a third transducer element, which fourth transducer element converts the respective energy forms of the second transducer element, in particular electrical and/or thermal energy, into further energy forms, in particular mechanical (kinetic/potential) and/or chemical energy and/or electromagnetic radiation. In this case, preferably elements having high thermal expansion, inflatable bags, shape memory materials, thermo- and/or electrochemical cells and reactors and/or light- or radiation-emitting elements are part of the fourth transducer element. The conversion of the energy forms of the second transducer element into further energy forms can be effected in this case by way of thermal expansion of solids, liquids or gases and/or memory effects and/or thermally or electrically influenced chemical reactions and/or atomic and molecular energy absorption and emission.

In addition, all the transducer elements described can include components for direct local forwarding of the respective energy form and/or for application or coupling of energy to peripheral regions of the system. These may be in particular electrical, magnetic, thermal or acoustic conductors, components for demarcation or for transport of substances or mechanical connecting and coupling elements.

If a system according to the invention consists not only of a first and a second transducer element but also of a fourth transducer element that, by way of example, converts thermal energy of the second transducer element into kinetic energy, then the second and fourth transducer elements may be connected by a thermal conductor element.

The first transducer element of a system according to the invention is arranged in a first region that is physically at a distance from the regions of all the other second, third or fourth transducer elements and is not electrically conductively connected thereto.

If the first transducer element includes at least one electrical coil, then this may be connected to a frequency generator, an electrical AC voltage source and/or a device for sensing an electric current and/or a voltage, as a result of which a variable magnetic field can be generated and/or, in inverse form, a variable magnetic field can be converted into electrical signals and detected. If the first transducer element includes permanent magnets, then the movement or rotation thereof likewise means that a variable magnetic field or a rotary or alternating field is generable. To influence the field, the first transducer element may additionally include ferromagnetic components. Preferably, the first transducer element is used to produce a magnetic alternating field of defined frequency by virtue of at least one electrical coil of the first transducer element having an AC voltage applied to it.

If the second transducer element is arranged inside the magnetic alternating field produced by the first transducer element, a voltage of the same frequency is induced in the at least one electrical coil of the second transducer element and in this way the magnetic energy is converted into electrical energy, which can in turn be converted into other energy forms. These are preferably kinetic energy in the form of vibrations or sound waves that is able to be coupled into a shaped body, which may be part of the system, or into another body in peripheral regions of the system.

For this purpose, the third transducer element can be used, which particularly preferably should be a piezoelectric transducer element. A piezoelectric transducer element may be electrically conductively connected to the two poles of the electrical coil that forms the second transducer element, and can contract, that is to say periodically alter its length in at least one axial direction, in accordance with the frequency of the induced voltage. A third transducer element of this kind should in this case be held fixedly in a receptacle element that acts as a mechanical coupling link and allows the forwarding, emission and coupling of vibrations or sound waves to peripheral regions of the system.

Therefore, direct operation of the third transducer element is possible if the piezoelectric transducer element is used as an actuator as described. In this case, it may be arranged in a housing or shaped body with the electrical coil of the second transducer element.

During inverse operation of such a system according to the invention, voltages can be produced from external movements, vibrations or sound waves using the piezoelectric transducer element, and therefore the kinetic energy can be converted into electrical energy. If the electrical coil of the second transducer element and the piezoelectric transducer element of the third transducer element are electrically conductively connected to one another, an electric current flows through the electrical coil of the second transducer element and a corresponding magnetic field is generated. This magnetic field can be amplified with the soft magnetic core and the associated formation of a stray field.

Depending on the kinetics of the movement, the vibrations or the sound waves that are transmitted to the piezoelectric transducer, an electric alternating current or a specifically pulsed electric current or else an irregular flow of current and hence also a correspondingly variable magnetic field can result. The magnetic energy thereof in turn allows a voltage to be induced in the coil of the first transducer element and a corresponding energy conversion to be achieved. In this case, the first transducer element may be arranged outside a housing, a shaped body and also outside a body or cell tissue surrounding same.

The first transducer element may be connected to a measuring device for determining the induced voltage, so that determination of the electric current and/or the voltage of the first transducer element allows wireless external detection of mechanical and acoustic processes in peripheral regions of the third transducer element or else a defined wireless signal transmission that can be evaluated on the basis of frequency and/or amplitude and/or on the basis of signal form. The system according to the invention can therefore also be used as a sensor in which the signal transmission is effected by means of the energy transmission of the variable magnetic field produced.

It is also possible for the magnetic fields generated by the coil of the second transducer element in this manner to be detected by means of an externally arranged magnetic field sensor. As such, an application as a step counter, including gait or movement pattern detection, is possible, for example, if a part of the system according to the invention has been fixed to a living being. Such fixation may have taken place as a dual function, for example on a body prosthesis/orthosis, which has to be moved along with the living being anyway. In this connection, the force-fit and form-fit fixation of such a system according to the invention to a hole-shaped integration region on an osteosynthetic plate or other osteosynthetic component having a traditional hole arrangement, for example by means of screw connection in the case of applications in/on the fracture region, can allow a further sensory advantage besides the aforementioned stimulation of the implant's taking.

In the event of a defined physical stress on the fracture region, the system according to the invention produces signals defined at the osteosynthetic plate, for example, that are able to depict an integral expression of the progress or stagnation or even regression of the osteosynthesis.

In a system according to the invention, at least one third and/or fourth transducer element should be fixed by means of a receptacle element. Alternatively, it is possible for any combinations of second, third and fourth transducer elements to be fixed in a receptacle.

It is advantageous if at least one contour element is formed on the receptacle element. This allows an improved force-fit and form-fit connection to a shaped body and hence a transmission of force or moment and/or a transmission of thermal energy or else of other energy forms to the shaped body to be achieved. In this regard, it is beneficial if the receptacle element is integrated with at least one third and/or fourth transducer element in a shaped body or has at least part enclosed by the latter. The receptacle element should reach the surrounding shaped body or peripheral regions of the system, such as living cell tissue, for example, at least in the region in which the contour element(s) is/are formed. This is particularly advantageous if a shaped body is a prosthesis or an implant or an osteosynthetic plate or another osteosynthetic material, for example.

A receptacle element for at least one second, third or fourth transducer element should, depending on the purpose of use and configuration of the respective transducer element, advantageously be formed, at least in regions, from an acoustically conductive and/or elastically deformable material and/or be configured to be acoustically conductive or elastically deformable or thermally conductive or thermally insulating, electrically conductive or electrically insulating.

A receptacle element may, by way of example, be formed from an elastically deformable and thermally and electrically conductive material, in particular from titanium or titanium alloys.

Moreover, there is also the possibility of a receptacle element for one transducer element acting, at least in regions, as part of another transducer element, and the receptacle element of a second and/or third transducer element may thus, at least in regions, be configured as a fourth transducer element. This is in particular advantageous if the receptacle element forwards thermal energy and at the same time, at least in regions, converts it into kinetic energy by way of expansion or memory processes.

A system according to the invention as described above can be introduced into any non-ferromagnetic shaped body. This shaped body may also be electrically conductive. In addition, the system can also be introduced into further physically separate regions, such as human or animal organisms, fluidic systems, gas and liquid pressure vessels and structures and structural members. The system can moreover also be operated exclusively in one direction, that is to say either exclusively apply energy or exclusively act as a sensory-action element.

It is beneficial to operate a system according to the invention having a first transducer element that generates magnetic alternating fields at a frequency in the range from 10 Hz to 3000 Hz and preferably in the ranges 10 Hz to 50 Hz, 125 Hz to 175 Hz and 300 Hz to 3000 Hz and therefore induces voltages in these very frequency ranges in the electrical coil of at least one second transducer element. The magnetic alternating field of the first transducer element can be formed by using an electrical coil, to which AC voltage is applied, that is connected to a frequency generator or to a defined inverter controller, for example, or by using a moving permanent magnet. To operate the system, it is then necessary for the first transducer element to be brought just sufficiently close to the electrical coil, held in the receptacle element, of the second transducer element for a maximum distance not to be exceeded that makes it possible to ensure that a sufficiently large voltage can be induced in the electrical coil of the second transducer element. With an amplifier, e.g. with 10-fold gain, connected between the function generator and the electrical coil of the first transducer element, it is possible for the maximum distance to be made longer or for the effectiveness to be increased. The frequency generator can be operated sinusoidally and if need be at variable frequency. In principle, however, other signal forms for the operation of a frequency generator are also possible.

The field strength of the magnetic alternating field generated by the first transducer element can be influenced by means of the voltage on the frequency generator or by means of the amplifier. This influences not only the maximum distance but also the voltage induced in the electrical coil of the second transducer element and hence the energy transmitted thereto.

The voltage induced in the electrical coil of the second transducer element can, when a moving permanent magnet is used in the first transducer element, be influenced by the magnetic field strength thereof, the distance from the second transducer element and the kinetic energy acting on the permanent magnet. A defined polar orientation and direction of movement of the permanent magnet allows the direction of the generated magnetic field and hence the induced voltage and the electric current flowing through the electrical coil of the second transducer element to be influenced, which in turn can also influence a third transducer element in direction-dependent fashion.

According to the BIOT-SAVART law, the magnetic field strength at any spatial point around an electrical coil is directly proportional to the electric current flowing through the electrical coil. This also applies at the location of the electrical coil of the second transducer element according to the invention. If a core made of a soft magnetic material is additionally employed that is arranged inside the electrical coil, a very high level of magnetization can be achieved even at very low field strengths. This magnetization can additionally be influenced by the choice of core material. On the basis of the geometry of the core of soft magnetic material used, a demagnetizing field appears in the core that reduces the field strength in the core. This effect can consequently also be influenced by the core geometry. The effect obtained is a resultant magnetic flux density in the core that changes virtually linearly as the magnetic field increases. Moreover, the elongate shape produces an orientation of the field lines perpendicular to the coil turns, relatively independently of the direction of the magnetic field of the first transducer element. Since the coil geometry of the electrical coil of the second transducer element, i.e. the cross-sectional area of the turns, and the number of turns are invariable, the magnetic flux through this coil changes only in the event of a change in the magnetic flux density. The change in the magnetic flux density in the electrical coil of the second transducer element takes place in accordance with the magnetization curve of the core material and is caused by the periodic change in the field strength of the magnetic alternating field of the first transducer element that is used for excitation. The scaling factor between magnetic field strength and flux density is the permeability. According to the induction law, the voltage induced in the electrical coil is the same as the negative change in the electrical flux through the coil turns over time. This means that the induction voltage in the coil of the second transducer element in the arrangement described is merely dependent on the magnetic flux density change and hence both proportional to the excitation frequency of the electrical coil and proportional to the field strength of the magnetic field of the first transducer element. The magnetic field of the first transducer element is brought about by the flow of electric current in the coil thereof and is proportional to the electric current intensity. The electric current intensity is obtained according to the laws of electrical AC engineering from the voltage applied to the coil and the impedance. In this case, it is obtained from the nonreactive and inductive resistances of the coil. Ignoring the very small nonreactive component, as is achievable by means of a large wire diameter, for example, the electric current and hence also the magnetic field strength of the first transducer element are now dependent only on the inductive resistance and hence indirectly proportional to the excitation frequency. In summary, the direct proportionality of the induction voltage in the coil of the second transducer element and the excitation frequency, the direct proportionality of the induction voltage in the coil of the second transducer element and the magnetic field strength of the first transducer element and the indirect proportionality of the excitation frequency and the magnetic field strength of the first transducer element given the cited assumptions and simplifications in the coil of the second transducer element thus result in a constant induction voltage. If the excitation frequency is doubled, the voltage induced in the coil of the second transducer element would likewise double at constant magnetic flux density, but since the magnetic field strength of the first transducer element is halved as a result of the smaller flow of current, caused by the inductive resistance of the coil, the magnetic flux density also falls to half and the voltage induced in the coil of the second transducer element remains the same in total. This shows that a frequency independence, according to the invention, of the voltage induced in the coil of the second transducer element, and hence frequency-independent production of equal gradients, can be exploited.

If a fourth transducer element is used for the system according to the invention, which fourth transducer element allows the thermal energy obtained by means of a second transducer element as described above to be converted into kinetic energy, then the effect of the thermal expansion or a change in the geometry of a shape memory material can be exploited. To this end, the fourth transducer element used can be a component that changes its expansion or length in at least one dimension on the basis of temperature. This component may also be at least part of the aforementioned receptacle element. Such a fourth transducer element may also be thermally conductively connected via a thermal conductive element having a high thermal conductivity to at least subregions of the electrically shorted coil, or coil connected to an electrical load, of the second transducer element or to a ferromagnetic core associated with said coil. As a result, the fourth transducer element can be arranged at a particular location more flexibly and the desired effect on a shaped body or peripheral regions of the system can be achieved at that location.

The thermal energy of the second transducer element can alternatively be forwarded via a thermal conductive element to a location at which the thermal energy can be converted into chemical energy and/or, by means of thermochemical processes in a reactor or by way of reactions with parts and substances in peripheral regions of the system, can be used to manipulate the surroundings.

During the operation of the system according to the invention having a first transducer element, in which an electrical coil is used to convert the magnetic energy into electrical energy, the operating voltage of the coil can be overlaid with a voltage additionally induced in this coil by means of the activity of the piezoelectric transducer. The ratio of operating voltage to induced voltage may be relatively high and be e.g. 170V to 10 mV. Accordingly, a difference measurement for the voltages is advantageous in order to distinguish the obtained voltage signals from the operating voltage.

An analogous approach is beneficial for the measurement using an external magnetic field sensor as a receiver, in which case the overlaying of the magnetic field generated directly by the operation of the coil of the first transducer element with the magnetic field produced by the magnetic coil of the second transducer element on account of the activity of the piezoelectric transducer needs to be taken into consideration for the different measurement.

It may be advantageous to additionally subject the overlaid voltage or field signals to a frequency filtering.

If such a difference measurement for the voltages or field strengths is meant to be avoided, then that component of the magnetic field that is formed exclusively by virtue of the activity of the piezoelectric transducer and the electrical coil of the second transducer element with a core possibly arranged therein can be measured in the switched-off state of the first transducer element. This component may be influenced by the magnetic past history and/or the remanence of the core, for example. In this case too, the measurement can be taken, as described, either directly using a magnetic field sensor or by measuring the voltage induced in the coil of the first transducer element.

In the case of a system according to the invention, there is also the possibility of not connecting the second transducer element, that is to say in particular the electrical coil, to the third transducer element, which may be configured as a piezoelectric transducer, permanently, but rather of switching a connection thereof in externally triggered fashion. This can be achieved using a reed contact, for example. This allows the voltage on the piezoelectric transducer of the third transducer element to be maintained for longer if said piezoelectric transducer has had a mechanical force applied to it beforehand. When the electrical connection between the piezoelectric transducer and the electrical coil is completed, a larger electric current can flow over a shorter period. This can allow better detection of a measurement signal, since the intensity of the signal is increased and the time of occurrence is known as a result of the externally triggered circuit.

The material employed for the piezoelectric transducer of the third transducer element may be a piezoelectric material that is as soft as possible and has high hysteresis. Given a piezoelectric transducer (stack actuator) with the dimensions 3×3×2 mm$^3$ and an operating voltage of 100 V for the coil of the first transducer element (in trigger-switched mode), a lateral expansion of 22 μm can be achieved. The electrical capacitance of this piezoelectric transducer may be 25 nF. The blocking force that fixes the piezoelectric transducer in the receptacle element should be greater than 120 N.

When excited by an AC voltage, the piezoelectric transducer of the third transducer element performs a volume oscillation. The lateral contraction is performed according to the stiffness tensor. For a piezoelectric transducer polarized in the main direction of expansion, the transverse contraction can be obtained by multiplication by the Poisson's ratio (0.28 . . . 0.36). The dynamic stiffnesses of the piezo materials are very high and are usually in the region of more than 10 GPa. In a system according to the invention, the lateral expansion can be exploited. It can be transmitted along a thin plate-shaped receptacle element, which may preferably be formed from titanium or an appropriate titanium vanadium aluminum alloy. The piezoelectric transducer of the third transducer element may be integrated in this plate-shaped receptacle element by means of thermal fitting. The ferromagnetic core arranged inside the electrical coil of the second transducer element may likewise be integrated in the plate-shaped receptacle element by means of thermal fitting. This allows part of the oscillation wave propagation to take place not only via lateral webs/contour elements but also partly through the core material, it being possible to utilize the fact that steels and titanium have comparable acoustic characteristic impedances (steel e.g. 5900 Ns/m$^3$ vs. titanium 6100 Ns/m$^3$).

A magnetic alternating field generated by a first transducer element and having a magnetic field strength of approximately 2 kA/m can induce a voltage having an amplitude of at least 300 mV and a frequency of 300 Hz, for example, in the electrical coil of the second transducer element. Since the mechanical stress-strain response of a piezoelectric transducer made of soft piezo ceramic is still linear at low voltages, for example up to one thousandth of the operating voltage, a piezoelectric transducer operated in this manner can be employed in a system according to the invention for small power sound applications, such as structure-borne sound applications, for example.

A piezoelectric transducer as third transducer element can therefore be operated self-sufficiently in terms of energy and without internal control electronics using the system according to the invention.

A polarized piezo stack actuator as third transducer element has a linear relationship between electric field strength E and mechanical strain S in the region below saturation polarization. In the lower voltage or field strength region, up to approximately one third of the operating voltage, this also applies to operation counter to the polarization direction. During virtually steady-state operation at frequencies of less than 10 Hz, the rise in the V-S or E-S characteristic curve can deviate, however. The operating voltage is normally at the voltage corresponding to half the saturation field strength. The linear response is not influenced by the action of a constant externally acting force. Far below the resonant frequency of the piezoelectric transducer, the mechanical strain is frequency-independent when the voltage has a constant amplitude. The resonant frequency in the 33 direction of a described stack actuator is 660 kHz and therefore above the operating frequencies indicated as beneficial.

BRIEF DESCRIPTION OF THE DRAWINGS

The invention will be explained in more detail by way of example below. In the drawings:

FIG. 1.1 shows an example of a part of a system according to the invention for applying mechanical energy in a partially sectional view from the side;

FIG. 1.2 shows the example shown in 1.1 in a sectional view from the side with the ferromagnetic core visible;

FIG. 2.1 shows an example of a part of a system according to the invention for applying mechanical energy in cross section;

FIG. 2.2 shows the example shown in FIG. 2.1 in a view from the side;

FIG. 3.1 shows an example of a part of a system according to the invention for applying thermal energy with a thermal conductive element in cross section;

FIG. 3.2 shows the example shown in FIG. 3.1 in a view from the side;

FIG. 3.3 shows the example shown in FIG. 3.1 with an additional switching element in a view from the side;

FIG. 4.1 shows an example of a part of a system according to the invention, what is known as an integration component, for applying mechanical and/or thermal energy for the integration into a shaped body in cross section;

FIG. 4.2 shows the example of an integration component shown in FIG. 4.1 with marked integration regions in a view from above;

FIG. 4.3 shows the example of an integration component as shown in FIG. 4.1 with marked integration regions in a view from the side;

FIG. 4.4 shows the example of an integration component as shown in FIG. 4.1 integrated in a shaped body with marked integration regions in a view from above;

FIG. 5.1 shows an example of a system according to the invention with an integration component introduced vertically into a shaped body for application of mechanical energy with integration regions visible and two externally arranged coils as first transducer elements for generating at least one magnetic alternating field and also deflection vectors in a view from the side;

FIG. 5.2 shows an example of a system according to the invention with an integration component introduced horizontally into a shaped body for applying mechanical energy with the integration interface visible and two externally arranged coils as first transducer elements for generating at least one magnetic alternating field and also deflection vectors in a view from the side;

FIG. 5.3 shows an example of a system according to the invention as shown in FIG. 5.2 with sensors additionally arranged on the shaped body in a view from the side;

FIG. 5.4 shows an example of a system according to the invention as shown in FIG. 5.2 with sensors additionally arranged on the shaped body and also a sensory/porous test specimen arranged on the shaped body and an actuator/sensor/actuator arrangement in a view from the side;

FIG. 6.1 shows an example of a system according to the invention with an integration component introduced vertically into a shaped body for producing thermal energy and a transducer element for downstream conversion into mechanical energy, including a coil as first transducer element, in a view from the side;

FIG. 7.1 shows an example of a system according to the invention with an integration component introduced horizontally into a shaped body for applying mechanical energy to a receptacle unit for biological samples that is arranged on the shaped body and also two coils as first transducer elements that are arranged on two opposite sides of the shaped body and the receptacle unit, in a view from the side;

FIG. 7.2 shows an example of a system according to the invention with an integration component introduced vertically into a shaped body for applying mechanical energy to a receptacle unit for biological samples that is arranged on the shaped body and two coils as first transducer elements that are arranged on two opposite sides of the shaped body and the receptacle unit, in a view from the side;

FIG. 8.1 shows an example of a system according to the invention with an integration component for applying mechanical energy, which system is integrated in a shaped body configured as a hip prosthesis, and also an externally arranged coil as first transducer element and a sensor in a view from the side;

FIG. 8.2 shows an example of a system according to the invention with two integration components for producing thermal energy that are integrated in a shaped body configured as a hip prosthesis, two fourth transducer elements for downstream conversion of the thermal energy into mechanical energy and also an externally arranged coil as first transducer element and a sensor in a view from the side;

FIG. 9.1 shows an example of an osteosynthetic component/plate with a hole arrangement;

FIG. 9.2 shows an example of a system according to the invention with a hole arrangement in the integration region in a plan view;

FIG. 9.3 shows an example of a system according to the invention with the hole arrangement in the integration region in a view from the side;

FIG. 9.4 shows an example of the integration of a system according to the invention with a hole arrangement in the integration region on an osteosynthetic component/plate with a hole arrangement without screws in a plan view;

FIG. 9.5 shows an example of a system according to the invention with a hole arrangement in the integration region in a view from the side, which system has been embedded by means of thermal spraying, for example with a titanium vanadium aluminum alloy, FIG. 9.6 shows an example of the integration of a system according to the invention with a hole arrangement in the integration region on an osteosynthetic component/plate with a hole arrangement without screws (plan view), which system has been embedded by means of thermal spraying, for example with a titanium vanadium aluminum alloy;

FIG. 9.7 shows an example of the integration of a system according to the invention with an anchor-shaped integration interface in an osteosynthetic screw;

FIG. 9.8 shows an example of the integration of a system according to the invention with a radial integration interface in the form of a sleeve or a thermally sprayed plasma layer in an osteosynthetic screw.

DETAILED DESCRIPTION OF EMBODIMENTS OF THE INVENTION

FIG. 1.1 and FIG. 1.2 show an example of a system according to the invention in two views, in which, in a receptacle element 1, which is preferably made of titanium, an electrical coil 2 as second transducer element and a piezoelectric transducer element 15 as third transducer element, which is formed by means of multiple plate-shaped piezoelectric elements stacked above one another and is electrically conductively connected to the electrical coil 2 by electrical conductor elements 25 such that the piezoelectric transducer element 15 contracts or expands when a voltage is applied to the electrical coil 2 and the piezoelectric transducer element 15. Since at least the piezoelectric transducer element 15 is connected to the receptacle element 1 with a force fit and/or form fit, this alteration of the piezoelectric transducer element 15 results in a force effect or deformation of the receptacle element 1. This force effect or deformation can be used to couple vibrations or sound waves to a shaped body connected to the receptacle element 1 and enclosing it at least in regions, for example.

In order to improve this effect of the coupling, there are on the receptacle element 1, as shown in the depiction in FIG. 1.2, contour elements 1a that result in an improved form fit and a greater lever effect. In this example, the contour elements 1a are configured in nose-shaped fashion. Alternatively, other geometric shapes can be chosen for contour elements 1a, such as e.g. hook and/or angled-off elements or flanges.

In this example, the receptacle element 1 has a rectangular cross section. The piezoelectric transducer element 15 is enclosed by a ceramic layer 4 that is broken only by the electrical conductor elements 25 between the piezoelectric transducer element 15 and the electrical coil 2 and by means of which electrical and/or thermal insulation of the parts of the system is achievable.

Depicted beneath one another at the side of the receptacle element 1 are three variants of a first transducer element, the first variant of the first transducer element being formed from an electrical coil 9 for generating a magnetic alternating field. In the second variant, beneath said first variant, the first transducer element additionally also includes a ferromagnetic core 10.1 arranged in the electrical coil 9. In the case of the third variant, beneath said second variant, the ferromagnetic core 10.2 is arranged outside the electrical coil 9. The depicted variants of first transducer elements can alternatively also be used in combined fashion. Moreover, different arrangements of individual or multiple first transducer elements than the depicted lateral arrangement of the first transducer elements in relation to the receptacle element 1 are also possible.

The described variants of a first transducer element allow magnetic alternating fields of different frequency to be generated if the electrical coil 9 of a first transducer element is applied with an AC voltage, which can be produced by a frequency generator, not shown, for example. If the electrical coil 2 of a second transducer element is in the surroundings and in sufficient proximity to this magnetic alternating field, then a voltage is induced in said electrical coil. To increase the induced voltage, a ferromagnetic core 3 made of soft magnetic material is arranged in the coil 2. Since the piezoelectric transducer element 15 is electrically conductively connected to the electrical coil 2 by means of the electrical conductor elements 25, deformations of the piezoelectric transducer element 15 occur depending on the polarity and characteristic of the induced voltage, which can be influenced in accordance with Lenz's Law, said deformations being able to be transmitted via the receptacle element 1 and the fitted contour elements 1a to the surroundings and in particular to a connected shaped body, not depicted here, in the form of vibrations or sound waves.

As such, the system according to the invention allows energy to be wirelessly transmitted from a first region, which contains at least one first transducer element, to a second, physically separate region, which is not electrically conductively connected, having at least one second transducer element, and allows vibrations or sound waves to be emitted in this region by means of a third transducer element, configured as a piezoelectric transducer element 15, and to be transmitted to the surroundings and/or coupled to a connected shaped body by means of the receptacle element 1.

FIG. 2.1 and FIG. 2.2 show a more complex design for a part of a system according to the invention in two views. It can be seen that an electrical coil 2 as second transducer element encloses a ferromagnetic core 3, so that the latter is arranged inside the electrical coil 2. The electrical coil 2, the ferromagnetic core 3 and a part of the receptacle element 1 are enclosed by multiple cylinder-shaped ceramic layers 4 and 6 that have both an electrically and a thermally insulating effect. The ceramic layers 4 and 6 may be formed from dielectric ceramic materials, preferably zirconium oxide or aluminum oxide.

Above that, there is a layer 7 of molybdenum encasing these ceramic layers 4 and 6. This molybdenum layer 7 is enclosed by a sleeve 8 made from titanium that is joined to the layer 7 with a force fit, form fit and/or cohesively, with two end faces being open, so that the contour elements 1a or a thermal conductor 5, which is not depicted here, can protrude. The arrangement may, moreover have an integrated third transducer element, not depicted here, for example a piezoelectric transducer.

The integrated arrangement of the parts of the system according to the invention in the encapsulated manner described allows simple integration of said parts into a shaped body, not portrayed here, and the electrical and thermal insulation of individual system parts among one another and/or of the system parts in relation to peripheral regions of the system, and is subsequently referred to as a whole as integration component 28.

FIG. 3.1 and FIG. 3.2 show a further example of an integration component, that is to say of a more complex design of a part of a system according to the invention in two views, in which, again, a receptacle element 1 holds an electrical coil 2 as second transducer element with a form and/or force fit and, in turn, said electrical coil is enclosed by multiple cylinder-shaped ceramic layers 4 and 6 that have both an electrically and a thermally insulating effect. Above that, there is again a layer 7 of molybdenum encasing these ceramic layers 4 and 6 that is surrounded by a sleeve 8 made from titanium with a force fit, form fit and/or cohesively.

The electrical coil 2 and/or a ferromagnetic core 3, which cannot be seen, is connected to a thermal conductor element 5 that is routed to the outside from the receptacle element 1. This thermal conductor element 5 may be routed to the outside completely or only in regions in this case. The thermal conductor element 5 may be formed from a highly thermally conductive metal, such as e.g. aluminum, copper or an alloy of these elements. Alternatively, precious metals or titanium can be used for this. It may moreover be formed completely or in regions from a shape memory metal. A thermal conductor element 5 may also be formed by means of an element that alters its longitudinal extent on the basis of the respective temperature and from a material having a high thermal expansion coefficient.

If the parts of the depicted system are in a magnetic alternating field generated by means of first transducer elements not shown here, then the flow of current arising as a result of the voltage induced in the coil 2 when the coil 2 is shorted or loaded with an electrical load and the hysteretic losses in the ferromagnetic core and also the eddy currents in the electrically conductive parts of the system result in heating of the electrical coil 2 and of the ferromagnetic core 3. Thermal conduction in the thermal conductor element 5 means that these temperature increases also reach the regions of the shape memory metal or of the element that expands on heating, and thermal energy can be converted into mechanical energy.

If there is an additional thermally activable element 12 as fourth transducer element, in particular an actuator that converts thermal energy into mechanical energy and is made of a shaped memory metal, for example, then said element may be arranged outside the sleeve 8 and thermally conductively connected to the parts integrated in the sleeve 8, in particular the electrical coil 2 and the ferromagnetic core 3, by means of the thermal conductor element 5.

Such a fourth transducer element may alternatively be arranged inside the sleeve 8 and surrounded by the ceramic layers 4 and 6. In this case, it may be connected to the receptacle element 1 such that a movement in the event of a rise above or drop below a respective critical temperature or corresponding deformation of the receptacle element is possible.

FIG. 3.3 shows an example of an integration component 28 as shown in FIG. 3.1 and FIG. 3.2 with an additional switching element 26 that can be used to influence the time of the conversion of the energy of the magnetic alternating field of the first transducer element into thermal and/or electrical energy and/or the forwarding thereof to third and/or fourth transducer elements or peripheral regions of the system in externally triggered fashion.

In particular, a short circuit in the electrical coil 2 and/or the electrical connection between the electrical coil 2 and an electrical load, such as a filament, for example, and/or the connection between the electrical coil 2 and an integrated third transducer element, such as a piezoelectric transducer, for example, and/or the electrical connection to a fourth transducer element is/are able to be made or broken by means of a reed contact defined as switching element 26. As a result, the time at which thermal energy is produced in the second transducer element is also influenceable. Similarly, this allows, as set out in the general part of the description, the time of the discharge of a piezoelectric transducer, used for detection purposes and having mechanical impulses applied to it, via the coil 2 to be influenced.

In addition, externally triggered making or breaking of a thermal connection, for example between the thermal conductor 5 and a fault transducer element converting the thermal energy into mechanical energy, is also possible. To this end, the switching element 26 can include, for example in addition to a reed contact, a bimetallic component or be configured entirely as a bimetallic component that makes or breaks thermal and possibly additionally electrical contact on deformation.

FIG. 4.1 shows the cross section through a part of a system according to the invention as shown in FIG. 2.1 by way of example, said system preferably being suitable for integration in a shaped body and forming an integration component.

FIG. 4.2 and FIG. 4.3 show the integration component in a view from above and a view from the side, respectively. In this case, the integration regions 27 that make the connection between the part and the shaped body are framed by dashed lines. These can include parts of the receptacle unit 1 or contour element 1*a* formed thereon and parts of the sleeve 8. The shaped body can be connected to the integration regions 27 of the integration component using fitting means or clamping means, for example, but also using soldering or melting processes.

FIG. 4.4 shows a part of a shaped body 13 that has an integration component according to the invention as shown in FIGS. 4.1, 4.2 and 4.3 integrated in it. In this case, the integration regions 27 are again framed by a dashed line. In addition, it can be seen that the integration regions 27 of the integration component by means of which the connection to the shaped body 13 is made are in the regions of the contour elements 1*a* formed on the receptacle element 1.

FIGS. 5.1 and 5.2 reveal, by way of example, the mode of action of a system according to the invention having an integration component 28 integrated in a shaped body 13. In this case, the two electrical coils 9.1 and 9.2 as first transducer elements, which are connected to a frequency generator, not shown here, can be used to generate a magnetic alternating field that induces a voltage at the same frequency in an electrical coil 2, not shown here, of a second transducer element that is in the integration component 28, this in turn leading to the deformations of a piezoelectric transducer element 15 as third transducer element that were explained earlier. The arrows 29 shown are intended to clarify the respective direction of action of the applicable forces. The connection of the integration component 28 to the shaped body 13 via the integration regions 27, not shown here, transmits or couples the mechanical impulses produced by the acting forces to the shaped body 13 as waves or vibrations. The dashed frame around the electrical coil 9.2 is intended to indicate that said electrical coil can also be operated independently of the electrical coil 9.1 or else can be dispensed with completely.

In this case, FIG. 5.1 shows an integration component 28 introduced vertically into a shaped body 13, the coils 9.1 and 9.2 of the first transducer element likewise being arranged vertically, while FIG. 5.2 depicts an integration component 28 introduced horizontally into a shaped body 13 and having horizontally arranged coils 9.1 and 9.2 of the first transducer element.

FIG. 5.3 shows a system according to the invention as shown in FIG. 5.1, wherein the shaped body 13 additionally has sensors 18 fitted to it that allow monitoring or else regulation of the effect to be achieved. The sensors 18 employed may be acceleration sensors, temperature sensors, magnetic field sensors, electrical field probes or acoustic sensors, for example. In this case, the sensors 18 can pick up measurement signals in scalar or directionally dependent fashion. The influencing of the effect of the system can be achieved in this case either by means of conductor elements arranged directly between the sensors 18 and the parts of the integration module 28 or, as described in the general part, by wirelessly supplied signals from an external region.

FIG. 5.4 shows a system according to the invention as shown in FIG. 5.3 in which there are, on the shaped body 13, additionally a sensory-action porous body 30 and a sensor/actuator network 31 that acts thereon or interacts therewith and is depicted schematically.

In the surroundings of the sensory-action porous body 30, there may be liquids or gases, for example, that penetrate the porous body at least in part and have mechanical impulses, waves or vibrations applied to them by the system according to the invention. If physical properties of the surroundings, such as the pressure, the temperature or the flow behavior of these substances, change due to external effects, then this can lead to a sensitively altered reaction response by the substances contained in the sensory-action porous body 30 to the mechanical or acoustic excitation by means of the system according to the invention, which can in turn be detected by the sensor/actuator network 31 shown and thus allows sensitive measurements of the applicable physical variables.

FIG. 6.1 shows an example of a system according to the invention with a deformable element 32 as fourth transducer element, which is arranged on a shaped body 13 and is connected to an initiator element 33 capable of initiating the deformation of the deformable element 32. The deformable element 32 is depicted in dashes in the deformed shape 32*a*. In the shaped body 13, an integration component 28 has been introduced that is connected directly to the initiator element 33 by means of a conductor element, not depicted here, or the shaped body, which allows the energy produced in the integration component 28 during operation of the system to be forwarded to the initiator element 33 in direct or converted form. The connection may be of electrical, thermal, acoustic, mechanical, material or chemical nature depending on the type of the initiator element 33. By way of example, the initiator element 33 may be a locking element made of a material having a high thermal expansion coefficient that releases the stored energy of a prestressed spring element as deformable element 32 again during the thermally induced initiation process by affording the expansion. In addition, chemical reactors or inflatable bags can act as an initiator element 33.

The system according to the invention that is described here by way of example is particularly suitable as a reanchoring or reblocking system that restores the lost contact between the shaped body and the surrounding body or periphery thereof.

FIGS. 7.1 and 7.2 show two variants of a system according to the invention with a receptacle 21 for biological samples that is integrated in a shaped body 13. Two electrical coils 9.1 and 9.2 as first transducer elements are arranged on two opposite sides of the shaped body 13 and the receptacle 21. Inside the shaped body 13, there is an integration component 28. The two variants differ in the orientation of the electrical coils 9.1 and 9.2 and of the integration component 28 in relation to the receptacle 21, FIG. 7.1 depicting a horizontal arrangement and FIG. 7.2 depicting a vertical arrangement. The depicted system allows a biological sample contained in the receptacle 21 to be influenced by vibrations.

The two electrical coils 9.1 and 9.2 can, as indicated by the dashed frame around coil 9.2 in FIG. 7.2, also be operated independently of one another, alternately or with staggered timing, so that the direction of propagation of vibrations or sound waves coupled into the shaped body can be influenced. It is also possible for one of the coils to be used on its own. Such an arrangement of multiple electrical coils 9 of a first transducer element can also be used for other embodiments and applications for the invention.

In this example, there is also a sensor 18 that allows the effect of the system according to the invention, as already described previously, to be monitored and/or regulation to be realized.

FIGS. 8.1 and 8.2 are intended to clarify advantageous use options for systems according to the invention.

In FIG. 8.1 an integration component 28 for producing, forwarding and coupling mechanical energy is incorporated in a prosthesis for a hip as shaped body 13. Part of the prosthesis fits tightly against the femur 22.1. The ball of the prosthesis is held in the pelvis 22.2. Arranged at a distance outside the respective living being above the outer skin 23 is an electrical coil 9 as first transducer element. The magnetic alternating field generated by the coil 9 brings about, as described and explained previously, by means of an electrical coil 2 as second transducer element and a piezoelectric transducer 15 electrically connected thereto as third transducer element, the two transducer elements being situated in the integration component 28, the coupling of mechanical vibrations and waves into the prosthesis as the shaped body and into the peripheral regions thereof in a manner conveyed via a receptacle element 1 having contour elements 1a. This allows the ingrowth of the prosthesis into the bone tissue to be stimulated.

A later check on the setting of the prosthesis in the bone is also possible. To this end, the electrical coil 9 as an inversely operated first transducer element allows a magnetic alternating field or magnetic signal generated by the electrical coil 2 of the second transducer element to be detected and evaluated, for example. A magnetic alternating field or magnetic signal of this kind can arise if, for example owing to vibrations or deformations of the shaped body 13 in the form of the prosthesis, voltages are produced with a piezoelectric transducer element as third transducer element 15. The resultant flow of electric current through the electrical coil 2 connected directly to the piezoelectric transducer element then generates a magnetic alternating field that can be detected and evaluated by means of the coil 9 of the first transducer element.

For alternative applications such as component or structural member monitoring, such vibration or deformation of the sensory-action shaped body 13 can also be generated in defined fashion, for example as in the case of hardness tests with a Poldi/Baumann hammer or by means of other acoustic signal generators. This methodology can also detect alterations in the stress state of the shaped body per se and of its periphery and also in the joints between the shaped body and the periphery.

The measurement of the magnetic field generated by the coil 2 of the second transducer element can also be measured and subsequently evaluated using an externally arranged magnetic field sensor or a separate sensor coil as sensor 18.

In FIG. 8.2, two integration components 28 for producing and forwarding thermal energy are incorporated in a prosthesis for a hip as shaped body 13. Part of the prosthesis fits tightly against the femur 22.1. The ball of the prosthesis is held in the pelvis 22.2. Arranged at a distance outside the respective living being above the outer skin 23 is an electrical coil 9 as first transducer element. The magnetic alternating field generated by the coil 9 brings about, as described and explained previously, by means of the two second transducer elements that are in the two integration components 28, heating of at least parts of the integration components 28, in particular of the coils 2 and/or integrated ferromagnetic cores 3 thereof, by way of the principles of Joule heating and also hysteretic and eddy-current losses. The deformable elements 32 as fourth transducer elements allow at least some of this heat energy to be converted into kinetic energy. This allows reanchoring of the prosthesis in the bone tissue to be achieved, for example.

In the case of systems according to the invention, in particular in the examples described previously, a ferromagnetic core 3, arranged in the electrical coil 2, of a second transducer element can have a length of 6 mm and an external diameter of 2 mm, for example. The core material may be, by way of example, a soft magnetic material, which is commercially available under the tradename PERMENORM 5000H2, or a magnetically semi-hard material, which is commercially available under the tradename VACOZET 258. The former is a nickel/iron alloy having a saturation polarization of 1.55 T, and the latter is a cobalt/iron/nickel alloy having a remanence induction of 1.4 T and a coercive field strength of 1-5 kA/cm.

In systems according to the invention for producing thermal energy, the ferromagnetic core 3 of a second transducer element may be wound with a preferably shorted electrical coil 2.

An electrical coil 2 of a second transducer element may have been manufactured from a copper wire having a wire diameter of 0.18 mm and a number of turns N=100. Its length in the direction of the longitudinal axis may be 5-6 mm.

For the thermal and electrical insulation of the parts of the integration unit 28, it is beneficial to observe a thermal stability of from 1000° C. to 1600° C., a thermal conductivity of from 0.48 W/m-1K-1 to 2.1 Wm-1K-1, a thermal expansion of from 7×10-6 K-1 to 14×10-6 K-1, a specific electrical resistance of from 108 to 109 Ωcm and a dielectric strength of 5 kV/mm.

The magnetic alternating field needed for operating a system according to the invention and generated by the first transducer element can be produced by means of one or more moving permanent magnets and/or by means of an electrical coil or a combination of electrical coils that may have one or more associated ferromagnetic cores 10.

FIG. 9.1 shows an osteosynthetic plate having a hole arrangement 14.1, as is used for screwing together bone fracture elements, as an example of a shaped body 13.

FIG. 9.2 shows an acoustic excitation unit in a titanium sleeve 8 with screw-connection-shaped contour elements 1a arranged at both ends with a corresponding hole arrangement 14.2 in plan view as an example of a system according to the invention.

FIG. 9.3 shows an acoustic excitation unit in a titanium sleeve 8 with screw-connection-shaped contour elements 1a arranged at both ends with a corresponding hole arrangement 14.2 in a view from the side.

FIG. 9.4 shows a plan view in which the acoustic excitation unit depicted in FIGS. 9.2 and 9.3 in a titanium sleeve 8 with screw-connection-shaped contour elements 1a arranged at both ends with a corresponding hole arrangement 14.2 is placed onto the osteosynthetic plate 13 with a hole arrangement 14.1 depicted in FIG. 9.1 such that the two hole arrangements 14.1 and 14.2 are above one another with a form fit, and it is therefore possible for the two components to be screwed to one another and/or to the bone fracture ends with a force fit. (The hole arrangements 14.1 of FIG. 9.1 which are not associated with a hole arrangement 14.2 are shown as hole arrangements 14.) An osteostimulative, mechanoacoustic vibration emanating from the acoustic excitation unit arranged in a sleeve can thus be applied with a force fit to the osteosynthetic plate 13 and, by virtue of the latter being screwed to the bone fracture ends, directly to the bone. The osteosynthetic plate thus excites the mechanotransduction in the fracture region topically.

FIG. 9.5 shows an acoustic excitation unit, in this case embedded in a titanium sleeve 8, with screw-connection-shaped contour elements 1a arranged at both ends with a corresponding hole arrangement 14.2 in a view from the side, said acoustic excitation unit having been encased bioactively with a titanium vanadium aluminum alloy by means of thermal spraying.

In FIG. 9.6, the acoustic excitation unit depicted in FIG. 9.5 is placed, analogously to FIG. 9.4, onto the osteosynthetic plate 13 with a hole arrangement 14.1 depicted in FIG. 9.1 such that the two hole arrangements 14.1 and 14.2 are above one another with a form fit and therefore allow the two components to be screwed to one another and/or to the bone fracture ends with a force fit. (As in FIG. 9.4, the hole arrangements 14.1 of FIG. 9.1 which are not associated with a hole arrangement 14.2 are shown as hole arrangements 14.) An osteostimulative, mechanoacoustic vibration emanating from the acoustic excitation unit arranged in a sleeve can thus be applied with a force fit to the osteosynthetic plate 13 and, by virtue of the latter being screwed to the bone fracture ends, directly to the bone.

The osteosynthetic plate thus excites the mechanotransduction in the fracture region topically.

FIG. 9.7 depicts the integration of a system according to the invention with anchor-shaped integration regions 27 in an osteosynthetic screw (shaped body) 13 having one thread 24 arranged before and one arranged after the acoustic excitation unit (integration component) 28.

FIG. 9.8 depicts the integration of a system according to the invention with a radial integration interface in the form of a sleeve 8 or a thermally sprayed plasma layer in the hole 14.3 in an osteosynthetic screw (shaped body) 13 having one thread 24 arranged before and one arranged after the acoustic excitation unit (integration component) 28.

In FIGS. 9.7 and 9.8, an osteostimulative, mechanoacoustic vibration emanating from the acoustic excitation unit (integration component) 28, arranged in a sleeve, having one thread 24 arranged before and one after the integration component 28 can thus be applied with a force fit to the osteosynthetic screw 13 and, by virtue of the latter being screwed to the bone fracture ends, directly to the bone. The osteosynthetic screw thus excites the mechanotransduction in the fracture region topically.

All the components of a system according to the invention that are embodied as individual components in the examples, in particular the first, second, third and fourth transducer elements and the receptacle and conductor elements, may also be parts of a system according to the invention repeatedly and in combination.

LIST OF REFERENCE NUMERALS

1 Receptacle element
1a Contour elements
2 Electrical coil of a second transducer element
3 Ferromagnetic core of a second transducer element
4 First ceramic layer
5 Thermal conductor element
6 Second ceramic layer
7 Molybdenum layer
8 Titanium sleeve/titanium plasma cover
9 Electrical coil of the first transducer element
9.1 First electrical coil of the first transducer element
9.2 Second electrical coil of the first transducer element
10 Ferromagnetic core of a first transducer element
12 Thermally activable element/fourth transducer element
13 Shaped body
14.1 Holes in shaped body (e.g. in this case in osteosynthetic plate)
14.2 Holes in integration component
14.3 Holes in shaped body (e.g. in this case in osteosynthetic screw)
15 Piezoelectric transducer element/third transducer element
18 Sensors
21 Receptacle for biological samples
22.1 Femur
22.2 Pelvis
23 Outer skin
24 Thread
25 Electrical conductor elements
26 Switching element
27 Integration regions
28 Integration components
29 Directions of action of force
30 Sensory-action porous body
31 Sensor/actuator network
32 Deformable element/fourth transducer element
32a Deformed deformable element/fourth transducer element
33 Initiator element

What is claimed is:

1. A system for the wireless transmission of energy and/or signals between physically separate regions without electrically conductive connections, the conversion of the energy and/or signals into other energy forms and/or signal forms and the application and/or detection thereof in at least one peripheral region of the system, wherein the system comprises at least one first transducer element by which magnetic alternating fields and/or magnetic signal forms are generable and/or detectable, the first transducer element being arranged in a first region, and (a) at least one second transducer element that allows reciprocal, unidirectional or bidirectional conversion of energy of the magnetic alternating fields and/or of the magnetic signal forms into electrical energy and/or electrical signal forms, as well as at least one third transducer element that allows reciprocal, unidirectional or bidirectional conversion of the electrical energy and/or electrical signal forms into mechanical energy, the second transducer element and the third transducer element being arranged in a further region adjacent to the first region, or (b) at least one second transducer element by which the energy of the magnetic alternating fields generated by the first transducer element is convertible into thermal energy by hysteretic heating and/or eddy currents and/or by Joule heating of the second transducer element, as well as a thermal conductor element that forwards the thermal energy to a location of application, the second transducer element and the thermal conductor element being arranged in a further region adjacent to the first region, or (c) at least one second transducer element that allows reciprocal, unidirectional or bidirectional conversion of energy of the magnetic alternating fields and/or of the magnetic signal forms into electrical energy and/or electrical signal forms and/or thermal energy, as well as at least one fourth transducer element that is electrically and/or thermally conductively connected to the second transducer element and allows reciprocal, unidirectional or bidirectional conversion of the electrical energy and/or electrical signal forms and/or thermal energy into further energy forms, at least partially, and/or forwards these energy forms, the second transducer element and the fourth transducer element being arranged in a further region adjacent to the first region.

2. The system of claim 1, alternative (a) or alternative (c), wherein second, third or fourth transducer elements are fixed alone or together with other transducer elements in a receptacle element.

3. The system of claim 1, alternative (a), wherein the third transducer element is a piezoelectric transducer element.

4. The system of claim 1, wherein a ferromagnetic core is arranged on or in a second transducer element.

5. The system of claim 1, alternative (a), wherein the second transducer element and the third transducer element are directly electrically conductively connected.

6. The system of claim 1, alternative (a), wherein at least one third transducer element is configured as or contains a short-circuit path of a coil of the second transducer element.

7. The system of claim 1, alternative (c), wherein a fourth transducer element converts and/or forwards at least some of the energy of at least one second transducer element and/or of at least one third transducer element into other energy forms.

8. The system of claim 1, alternative (a) or alternative (c), wherein the second, third or fourth transducer elements are arranged to make a multiple conversion of magnetic energy into electrical, mechanical, kinetic energy and/or thermal energy achievable.

9. The system of claim 1, wherein a first transducer element is an electrical coil having a ferromagnetic core, the ferromagnetic core being arranged in and/or on the electrical coil.

10. The system of claim 1, wherein a first transducer element comprises a combination of multiple coils that have one or more associated ferromagnetic cores made of the same or different materials.

11. The system of claim 1, wherein a receptacle element comprises at least one contour element present on it or the receptacle element is formed from an elastically deformable or acoustically conductive material.

12. The system of claim 1, wherein at least part of the second transducer element, the third transducer element and/or the fourth transducer element is enclosed by a shaped body.

13. The system of claim 12, wherein the shaped body is a prosthesis, an orthosis, an implant or an osteosynthetic aid.

14. The system of claim 12, wherein the shaped body comprises at least one associated sensor or sensory-action body.

15. The system of claim 12, wherein the shaped body comprises on it at least one receptacle for holding a sample.

16. The system of claim 1, wherein each first transducer element provides magnetic fields and signal forms at frequencies in a range of from 10 Hz to 3000 Hz.

17. The system of claim 1, wherein each first transducer element comprises at least one electrical coil to which a constant AC voltage is applied and at least one of the second, third or fourth transducer elements allows the conversion of the energy of the magnetic alternating fields and/or of the magnetic signal forms of the first transducer element into electrical energy and/or electrical signal forms and/or further energy or signal forms such that the last transducer element in a cascade realizes a physical gradient independently of frequency.

18. The system of claim 1, wherein the signals generated by at least one of the second, third or fourth transducer elements are recordable by a sensor, the sensor being arranged in the first region or in a further region that does not contain the transducer elements.

19. The system of claim 18, wherein the sensor is a sensor for detecting magnetic fields.

20. The system of claim 19, wherein the sensor is a sensor coil which coincides with at least one of electrical coils of the first transducer element.

* * * * *